US012730033B2

(12) United States Patent
Hurich et al.

(10) Patent No.: US 12,730,033 B2
(45) Date of Patent: Sep. 8, 2026

(54) DETECTING PROBLEMS OF A LASER BEAM OF A LASER SYSTEM

(71) Applicant: Alcon Inc., Fribourg (CH)

(72) Inventors: Joerg Michael Hurich, Lauf an der Pegnitz (DE); Frank Peter Meinhard, Heroldsberg (DE); Annelene Konz, Hollfeld (DE)

(73) Assignee: Alcon Inc., Fribourg (CH)

( * ) Notice: Subject to any disclaimer, the term of this patent is extended or adjusted under 35 U.S.C. 154(b) by 0 days.

(21) Appl. No.: 19/044,692

(22) Filed: Feb. 4, 2025

(65) Prior Publication Data

US 2025/0264371 A1 Aug. 21, 2025

Related U.S. Application Data

(60) Provisional application No. 63/556,123, filed on Feb. 21, 2024, provisional application No. 63/556,107, filed on Feb. 21, 2024, provisional application No. 63/556,113, filed on Feb. 21, 2024.

(51) Int. Cl.

| | |
|---|---|
| ***G01M 11/02*** | (2006.01) |
| ***A61F 9/008*** | (2006.01) |
| ***G01J 1/42*** | (2006.01) |

(52) U.S. Cl.

CPC ..... *G01M 11/0264* (2013.01); *A61F 9/00814* (2013.01); *A61F 9/0084* (2013.01); *G01J 1/4257* (2013.01); *G01M 11/0207* (2013.01); *G01M 11/0221* (2013.01); *A61F 2009/00844* (2013.01); *A61F 2009/00855* (2013.01)

(58) Field of Classification Search

CPC ......... G01M 11/0264; G01M 11/0207; G01M 11/0221; G01M 11/0278; A61F 2009/00855; A61F 2009/00897; A61F 2009/00844; A61F 9/00806; A61F 9/00814; A61F 9/0084; G01J 1/4257; G01J 2001/4261

See application file for complete search history.

(56) References Cited

U.S. PATENT DOCUMENTS

| | | | | |
|---|---|---|---|---|
| 5,460,627 A * | 10/1995 | O'Donnell, Jr. ..... | B23K 26/702 606/4 |
| 6,559,934 B1 * | 5/2003 | Yee ...................... | B23K 26/705 606/4 |
| 6,666,855 B2 * | 12/2003 | Somani ............... | A61F 9/00814 250/252.1 |
| 8,385,618 B2 * | 2/2013 | Youssefi ............... | G01J 1/4257 382/128 |

(Continued)

*Primary Examiner* — Gordon J Stock, Jr.

(57) ABSTRACT

In certain embodiments, an ophthalmic laser system include a laser system, imaging system, and computer. The laser system accesses a planned test pattern of a planned laser spot having a planned beam feature and directs a laser beam towards a test target located at a target plane according to the planned test pattern to yield an actual test pattern of an actual laser spot having an actual beam feature. The imaging system includes one or more digital cameras that generate a digital image of the actual test pattern of the actual laser spot. The computer analyzes the digital image to compare the actual laser spot to the planned laser spot, to detect a deviation of the actual beam feature from the planned beam feature, to identify an issue indicated by the deviation, and to provide output in response to the issue.

19 Claims, 18 Drawing Sheets

(56) References Cited

U.S. PATENT DOCUMENTS 8,968,279 B2 * 3/2015 Arnoldussen ....... A61F 9/00804
606/4
9,352,415 B2 * 5/2016 Sluyterman van Langeweyde .....
B23K 26/60
9,592,155 B2 * 3/2017 Chernyak .............. A61B 18/20
10,648,855 B2 * 5/2020 Kojo .................... B23K 26/032
11,726,032 B2 * 8/2023 Paudel ............... G01M 11/0278
356/432
11,883,328 B2 * 1/2024 Riedel ................. A61F 9/00804
11,896,526 B2 * 2/2024 Bareket ................... A61F 9/008
2020/0324465 A1 * 10/2020 Deruyck ............... B29C 64/153
2025/0262092 A1 * 8/2025 Hurich .................... A61F 9/008
2025/0264370 A1 * 8/2025 Hurich ............... G01M 11/0264
2026/0056050 A1 * 2/2026 Konz ................... A61B 3/0008

* cited by examiner

DETECTING PROBLEMS OF A LASER BEAM OF A LASER SYSTEM

TECHNICAL FIELD

The present disclosure relates generally to laser systems, and more particularly to detecting problems of a laser beam of a laser system.

BACKGROUND

Surgical laser systems utilize laser beams to perform medical procedures. The laser beam must be accurate and precise in order to perform safe and effective surgery. However, the surroundings of a system, movement of the system, and even routine usage of the system can affect the accuracy and precision of the system. In some cases, the optical devices of the system may fail to operate properly and cause the system to yield a laser beam of the wrong diameter and shape. Accordingly, it is important to detect any problems with the laser system.

Known techniques for detecting problems with laser systems include relying on a human technician to irradiate a test target and check the resulting laser spots. This technique, however, is slow and subject to human error.

BRIEF SUMMARY

In certain embodiments, an ophthalmic laser system includes a laser system, imaging system, and computer. The laser system accesses a planned test pattern of planned laser spots and directs a laser beam towards a test target located at a target plane according to the planned test pattern to yield an actual test pattern of actual laser spots on the test target. The actual laser spots correspond to the planned laser spots. The laser system includes a laser source that generates the laser beam and a scanner that guides the laser beam towards the test target. The imaging system has a digital camera that generates a digital image of the actual test pattern. The computer analyzes the digital image to: compare the actual test pattern to the planned test pattern; detect a deviation of the actual from the planned test pattern; identify an issue indicated by the deviation; and provide output in response to the identified issue.

Embodiments may include none, one, some, or all of the following features:

- The computer analyzes the digital image by: determining grayscale values of pixels of the digital image; identifying a subset of grayscale values that represent the actual laser spots; and ascertaining the actual test pattern according to the subset of grayscale values.
- The computer analyzes the digital image by ascertaining a dimension present in the actual test pattern according to a mathematical relationship between length and a number of pixels of the digital image.
- The planned laser spots are arranged along a first planned axis orthogonal to a second planned axis, and the actual laser spots are arranged along a first actual axis and a second actual axis. The deviation is that the first actual axis is not orthogonal to the second actual axis. The issue indicated by the deviation may be that the scanner is misaligned or that the laser beam and the target plane are misaligned.
- The planned laser spots include a first planned laser spot at a planned spot separation from a second planned laser spot, and the actual laser spots include a first actual laser spot at an actual spot separation from a second actual laser spot. The deviation is that the actual spot separation is not the same as the planned spot separation. The issue indicated by the deviation may be that the scanner cannot properly guide the laser beam to yield the planned spot separation.
- The planned test pattern has a planned geometric shape, and the actual test pattern has an actual geometric shape. The deviation is that the actual geometric shape is not the same as the planned geometric shape. The issue indicated by the deviation may be that the laser beam and the target plane are misaligned or that the scanner is misaligned.
- A planned laser spot of the planned test pattern has a planned sharpness, and an actual laser spot of the actual test pattern has an actual sharpness. The deviation is that the actual sharpness does not satisfy the planned sharpness. The issue indicated by the deviation may be that the system is experiencing an unwanted vibration or that the laser system cannot properly focus the laser beam.
- The computer provides the output in response to the identified issue by providing a warning indicating a problem with the laser system.
- The computer provides the output in response to the identified issue by sending a command to the laser system that addresses the issue.
- The computer provides the output in response to the identified issue by calculating a correction to remove the deviation and generating a command to instruct the scanner to implement the correction.
- The issue indicated by the deviation is that the scanner is guiding the laser beam with a distance error, and the output is a command that adjusts the scanner to remove the distance error.
- The imaging system includes a digital microscope.
- The computer accesses previous actual test patterns, analyzes the previous actual test patterns, and detects a trend of a previous issue with the laser system in accordance with the previous actual test patterns.
- The digital camera generates a digital calibration image of a calibration pattern that shows a known length. The computer determines grayscale values of pixels of the digital calibration image (e.g., as calibration grayscale values), identifies a subset of the grayscale values that represent the known length, and determines a mathematical relationship between the known length and a number of pixels.
- The computer can instruct the laser system by sending a command to the laser system. The computer may instruct the laser system to direct the laser beam towards the test target located at the target plane according to the planned test pattern, to control the laser source to generate the laser beam, or to control the scanner to implement a correction to remove a deviation
- The computer is coupled to the laser system via a wired, wireless, and/or telecommunication network connection.

In certain embodiments, an ophthalmic laser system includes a laser system, imaging system, and computer. The laser system accesses a planned test pattern of planned laser spots and directs a laser beam towards a test target located at a target plane according to the planned test pattern to yield an actual test pattern of actual laser spots on the test target. The actual laser spots correspond to the planned laser spots. The laser system includes a laser source that generates the laser beam and a scanner that guides the laser beam towards the test target. The imaging system has a digital camera that generates a digital image of the actual test pattern. The computer analyzes the digital image to: determine grayscale values of pixels of the digital image; identify the subset of grayscale values that represent the actual laser spots; ascertain the actual test pattern according to the subset of grayscale values; and compare the actual test pattern to the planned test pattern. The computer ascertains an actual dimension present in the actual test pattern according to a mathematical relationship between length and a number of pixels. The computer detects a deviation of the actual dimension present in the actual test pattern from a planned dimension present in the planned test pattern and sends a command to the scanner to address the deviation.

Embodiments may include the following feature:

The computer sends the command to the scanner by calculating a correction to remove the deviation and generating the command to instruct the scanner to implement the correction.

In certain embodiments, an ophthalmic laser system includes a laser system, imaging system, and computer. The laser system accesses a planned test pattern of a planned laser spot having a planned beam feature and directs a laser beam towards a test target located at a target plane according to the planned test pattern to yield an actual test pattern of an actual laser spot on the test target. The actual laser spot corresponds to the planned laser spot and has an actual beam feature. The laser system has a laser source that generates the laser beam and one or more beam control devices that guide the laser beam towards the test target. The imaging system includes one or more digital cameras that generate a digital image of the actual test pattern of the actual laser spot. The computer analyzes the digital image to compare the actual laser spot to the planned laser spot, to detect a deviation of the actual beam feature from the planned beam feature, to identify an issue indicated by the deviation, and to provide output in response to the issue.

Embodiments may include none, one, some, or all of the following features:

The computer analyzes the digital image by determining grayscale values of pixels of the digital image, identifying a subset of the grayscale values that represent the actual laser spot, and ascertaining the actual beam feature according to the subset of the grayscale values that represent the actual laser spot.

The computer analyzes the digital image by ascertaining a dimension of in the actual laser spot according to a mathematical relationship between length and a number of pixels of the digital image.

The computer analyzes the digital image by ascertaining the length of one or more diameter chords of the actual laser spot.

The computer analyzes the digital image by ascertaining a first length of a first diameter chord of the actual laser spot, and ascertaining a second length of a second diameter chord of the actual laser spot, where the second diameter chord is orthogonal to the first diameter chord.

The computer detects the deviation of the actual beam feature from the planned beam feature by ascertaining an actual diameter of the actual laser spot, comparing the actual diameter to a planned diameter of the planned laser spot, and determining whether the actual diameter differs from the planned diameter.

The computer detects the deviation of the actual beam feature from the planned beam feature by ascertaining an actual shape of the actual laser spot, comparing the actual shape to a planned shape of the planned laser spot, and determining whether the actual shape differs from the planned shape.

The computer detects the deviation of the actual beam feature from the planned beam feature by ascertaining an actual sharpness of the actual laser spot, comparing the actual sharpness to a planned sharpness of the planned laser spot, and determining whether the actual sharpness differs from the planned sharpness.

The computer identifies the issue indicated by the deviation by identifying a beam control device of the one or more beam control devices that fails to properly guide the laser beam to the test target. The computer may provide the output in response to the issue by instructing the beam control device to properly guide the laser beam to the test target.

The computer identifies the issue indicated by the deviation by determining that the laser beam is misaligned with the target plane. The computer may provide the output in response to the issue by instructing the laser system to align the laser beam with the target plane.

The computer provides the output in response to the issue by providing a warning indicating a problem with the laser system.

The computer provides the output in response to the issue by sending a command to the laser system that addresses the issue.

The computer provides the output in response to the issue by calculating a correction to remove the deviation and generating a command to instruct the laser system to implement the correction.

The imaging system includes a digital microscope.

The computer accesses previous actual test patterns, analyzes the previous actual test patterns, and detects the trend of a previous issue with the laser system in accordance with the previous actual test patterns.

The digital cameras generate a digital calibration image of a calibration pattern that shows a known length, and the computer determines a mathematical relationship between the known length and a number of pixels of the digital calibration image. The computer may determine the mathematical relationship by: determining calibration grayscale values of the pixels of the digital calibration image; identifying a subset of the calibration grayscale values that represent the known length; and determining the mathematical relationship between the known length and the number pixels according to the subset of calibration grayscale values that represent the known length.

In certain embodiments, ophthalmic laser system includes an auxiliary light system, laser system, imaging system, and computer. The auxiliary light system directs auxiliary light towards a test target located at a target plane according to a planned test pattern to yield one or more actual auxiliary spots of an actual test pattern on the test target. The planned test pattern indicates one or more planned auxiliary spots located relative to a planned laser spot in a predetermined manner. An actual auxiliary spot corresponds to a planned auxiliary spot. The laser system directs a laser beam towards the test target according to the planned test pattern to yield an actual laser spot of the actual test pattern on the test target. The actual laser spot corresponds to the planned laser spot of the planned test pattern. The imaging system has one or more digital cameras that generate a digital image of the actual test pattern. The computer analyzes the digital image to compare the actual test pattern to the planned test pattern, to detect a deviation of the actual test pattern from the planned test pattern, to identify an issue indicated by the deviation, and to provide output in response to the issue.

Embodiments may include none, one, some, or all of the following features:

The computer analyzes the digital image by: determining grayscale values of pixels of the digital image; identifying a subset of grayscale values that represent the one or more actual auxiliary spots; and analyzing the one or more actual auxiliary spots according to the subset of grayscale values.

The computer analyzes the digital image by ascertaining a dimension of an actual auxiliary spot according to a mathematical relationship between length and a number of pixels of the digital image.

The computer detects the deviation of the actual test pattern from the planned test pattern by determining whether the one or more actual auxiliary spots are located relative to the actual laser spot in the predetermined manner.

The auxiliary light comprises an aiming beam, and the planned test pattern indicates that the planned auxiliary spot corresponding to the aiming beam is located at the planned laser spot. The computer detects the deviation of the actual test pattern from the planned test pattern by determining whether the actual auxiliary spot corresponding to the planned auxiliary spot is located at the actual laser spot. The computer may detect the deviation by determining the length of the deviation between the actual auxiliary spot and the actual laser spot. The computer may provide the output by instructing the auxiliary light system to move the aiming beam such that the actual auxiliary spot is located at the actual laser spot.

The auxiliary light comprises a fixation beam, and the planned test pattern indicates that the planned auxiliary spot corresponding to the fixation beam is located at the planned laser spot. The computer detects the deviation of the actual test pattern from the planned test pattern by determining whether the actual auxiliary spot corresponding to the planned auxiliary spot is located at the actual laser spot. The computer may detect the deviation by determining the length of the deviation between the actual auxiliary spot and the actual laser spot. The computer may provide the output by instructing the auxiliary light system to move the aiming beam such that the actual auxiliary spot is located at the actual laser spot.

The auxiliary light comprises distance beams, and the planned test pattern indicates that the planned auxiliary spots corresponding to the distance beams are superimposed. The computer detects the deviation of the actual test pattern from the planned test pattern by determining whether the actual auxiliary spots are superimposed. The computer may detect the deviation by determining the length of the deviation between the actual auxiliary spots. The computer may provide the output by instructing the auxiliary light system to move the distance beams such that the actual auxiliary spots are superimposed.

The computer provides the output in response to the issue by providing a warning indicating a problem with the laser system.

The computer provides the output in response to the issue by sending a command to the laser system that addresses the issue.

The computer provides the output in response to the issue by calculating a correction to remove the deviation and generating a command to instruct the laser system to implement the correction.

The imaging system includes a digital microscope.

The computer accesses previous actual test patterns, analyzes the previous actual test patterns, and detects the trend of a previous issue with the laser system in accordance with the previous actual test patterns.

The digital cameras generate a digital calibration image of a calibration pattern that shows a known length, and the computer determines a mathematical relationship between the known length and a number of pixels of the digital calibration image. The computer may determine the mathematical relationship by: determining calibration grayscale values of the pixels of the digital calibration image; identifying a subset of the calibration grayscale values that represent the known length; and determining the mathematical relationship between the known length and the number pixels according to the subset of calibration grayscale values that represent the known length.

DESCRIPTION OF EXAMPLE EMBODIMENTS

Figure 1:
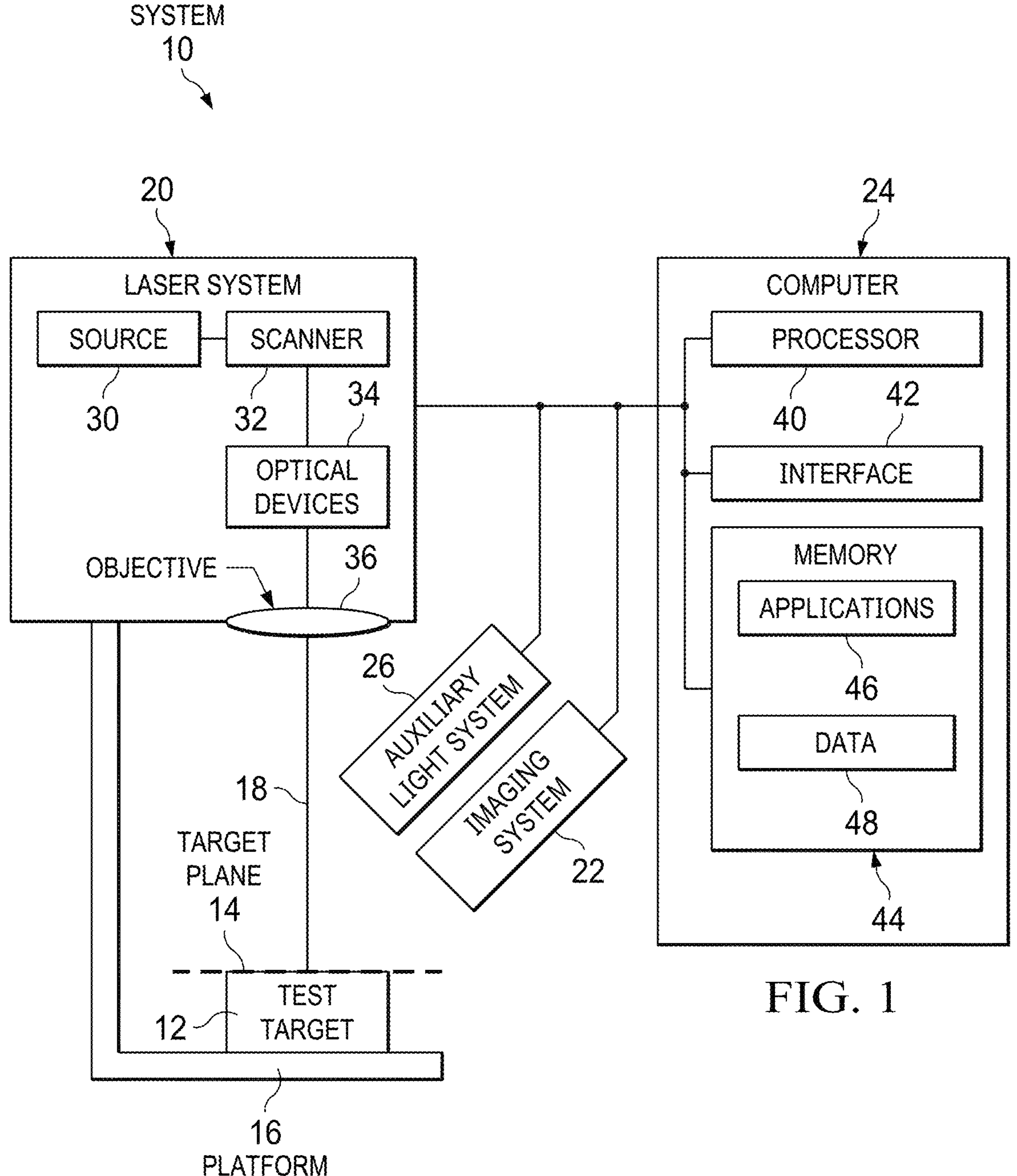
FIG. 1 illustrates an example of a system that detects problems with a laser system, according to certain embodiments.

Referring now to the description and drawings, example embodiments of the disclosed apparatuses, systems, and methods are shown in detail. The description and drawings are not intended to be exhaustive or otherwise limit the claims to the specific embodiments shown in the drawings and disclosed in the description. Although the drawings represent possible embodiments, the drawings are not necessarily to scale and certain features may be simplified, exaggerated, removed, or partially sectioned to better illustrate the embodiments.

Laser beam accuracy and precision is important for surgical systems to perform safe and effective surgery. Accordingly, certain embodiments described herein detect issues with features of the laser beam. In the embodiments, a surgical system includes a laser system that directs a laser beam to a test target to yield a laser spot on the test target. An imaging system captures a digital image of the laser spot. A computer analyzes the digital image to detect deviations of actual features of the laser spot from the planned features, e.g., detect whether the actual laser spot has the planned diameter and shape. In certain embodiments, the computer automatically sends a command to the laser system to correct the deviation.

Certain embodiments detect and correct problems faster and more reliably than a human can. For example, the computer may be programmed to check for problems automatically and periodically. As another example, the computer may automatically send instructions to a laser or light system to correct a problem. As another example, the computer may analyze results from previous checks to assess the laser performance over time and predict future problems. As yet another example, the computer may document the results and automatically send a report of the results.

FIG. 1 illustrates an example of a system 10 that detects problems with a laser system 20, according to certain embodiments. In the example, system 10 uses a test target 12 located at the target plane 14 to detect problems. System 10 includes a platform 16, laser system 20, imaging system 22, computer 24, and auxiliary light system 26 coupled as shown, where the couplings may represent a wired, wireless, telecommunications network, and/or other suitable communication connection. Laser system 20 includes a laser source 30, scanner 32, optical devices 34, and an objective 36, coupled as shown. Computer 24 includes a processor 40, interface 42, and memory 44, which stores applications 46 and data 48, coupled as shown.

According to an example of operation, laser system 20 accesses a planned test pattern that has a planned laser spot. Laser source 30 generates a laser beam, and scanner 32 directs the laser beam towards test target 12 according to the planned test pattern to yield an actual laser spot on test target 12. Imaging system 22 includes one or more digital cameras that generate a digital image of the actual laser spot. Computer 24 analyzes the digital image to compare the actual laser spot to the planned laser spot and to detect deviations of the actual from the planned laser spot. Computer 24 identifies an issue indicated by the deviations and provides output in response to identifying the issue.

For ease of explanation, the embodiments are described using the following example xyz-coordinate system, which may be regarded as the coordinate system of system 10, although any suitable coordinate system may be used. In the example, the z-axis is aligned with the optical axis of laser system 20, and the xy-plane is orthogonal to the z-axis and may be located at, e.g., target plane 14. Geometrical features (e.g., separation, length, direction, diameter, or shape) may be located in any suitable portion of the xyz-coordinate system. For example, a separation (or other geometrical feature) may be in an xy-plane, along the z-axis, or in a plane that is not orthogonal to the z-axis. In addition, the position of an object may refer to the location and/or orientation of the object.

The System. System 10 may be any suitable laser system that directs a laser beam 18 towards a target. In certain embodiments, system 10 may be a laser surgical system that performs surgical procedures on humans, such as an ophthalmic surgical system that performs surgical procedures on human eyes. Examples of such systems include cataract, refractive, vitreoretinal, or other ophthalmic surgical system.

Test Target. Turning to the components of FIG. 1, test target 12 is located at target plane 14 and may be supported by platform 16. Target plane 14 is the region where laser system 20 is designed to yield laser spots of test patterns and may represent the treatment plane. In some cases, target plane 14 may designate the z=0 plane. Test target 12 located at target plane 14 indicates where the laser spots will appear for the intended targets of laser system 20, e.g., a surgical site of human tissue such as the eye. Or stated another way, the distance from the laser system 20 to the target plane 14 may correspond to an expected or average distance from the laser system 20 to the surgical site when performing the surgery on human tissue (e.g., an eye).

Test target 12 comprises a photosensitive material or sensor that undergoes a visible change where a light beam interacts with target 12 to indicate where the beam interacted with plane 14. The visible change may be a change in color, where "color" includes chromatic and achromatic colors. For example, the material may be one color (a "non-radiated color") if there is no interaction, but changes to another color (an "irradiated color") if a beam interacts with it. Examples of test target 12 include photographic paper, metal foil, conversion screens, and polymethyl methacrylate (PMMA) material. In certain embodiments, test target 12 may comprise material that reflects a light beam to yield a digital image that indicate where the beam was reflected. In certain embodiments, the test target 12 may include a thin paper or material that may form a hole or void in the material when contacted by a laser beam, and the hole may be representative of a change in color.

Laser System. Laser system 20 directs a laser beam 18 towards test target 12 according to a test pattern, where laser source 30 generates the beam 18 and scanner 32 guides the beam 18 towards test target 12. Examples of laser source 30 include excimer and femtosecond lasers. The laser beam 18 may have any suitable pulse duration, such as on the order of nanoseconds, picoseconds, femtoseconds, or attoseconds. The laser beam 18 may have any suitable wavelength, such as in the range of 150 nanometers (nm) to 20 micrometers (μm). Examples of ranges include the ultraviolet (e.g., in the range of 180 to 400 nm, such as 190 to 195 nm or 345 to 355 nm), visible, or infrared wavelength (e.g., in the range of 1050 to 1250 or 1250 to 1500 nm). The laser beam 18 may ablate, incise, or photo-disrupt a target.

Scanner 32 transversely and/or longitudinally directs the focal point of a laser beam 18 towards a target. The transverse direction refers to directions orthogonal to the direction of beam propagation, i.e., the x- and y-directions. Scanner 32 may transversely direct the laser beam 18 in any suitable manner, e.g., using a pair of galvanometrically-actuated scanner mirrors or an electro-optical crystal. The longitudinal direction refers to the direction of the laser beam 18 propagation, e.g., the z-direction. Scanner 32 may longitudinally direct the laser beam 18 in any suitable manner, e.g., using a longitudinally adjustable lens, a lens of variable refractive power, or a deformable mirror that can control the z-position of the focal point.

One or more optical devices 34 direct the laser beam 18 from laser system 20 towards focusing objective 36 and may be located prior to, within, and/or after scanner 32. An optical device 34 can act on (e.g., transmit, reflect, refract, diffract, collimate, condition, shape, focus, modulate, and/or otherwise act on) a laser beam 18. Examples of optical devices 34 include a lens, prism, mirror, diffractive optical element (DOE), holographic optical element (HOE), and spatial light modulator (SLM).

In certain embodiments, optical devices 34 may include one or more beam control devices that control or adjust one or more features of a laser beam. Examples of beam control devices include beam expanders, collimators, beam shapers (such as diffractive beam shapers), beam scanners, and other optical devices that can control or adjust beam features. Laser beam features may include, e.g., the diameter and/or shape of the cross-section of the laser beam. In the illustrated example, the focusing objective 36 focuses the focal point of the laser beam 18 towards the test target 12 at the target plane 14.

Imaging System. Imaging system 22 includes one or more digital cameras or other optical sensors that can generate a digital image of laser or auxiliary spots on test target 12. In general, a digital camera or other optical sensors detect light from an object and generate a signal in response to the light. The signal carries digital image data that can be used to generate the digital image of the object. Examples of cameras include a charged-coupled device (CCD), video, complementary metal-oxide semiconductor (CMOS) sensor (e.g., active-pixel sensor (APS)), line sensor, and optical coherence tomography (OCT) camera. Imaging system 22 may include one camera that provides a two-dimensional image of target 12 or may include stereoscopic cameras that provide a stereoscopic three-dimensional image of target 12. In certain embodiments, imaging system 22 includes a digital microscope with one or two cameras that can provide a magnified image of target 12.

Auxiliary Light System. Auxiliary light system 26 directs light (e.g., a laser beam or illumination light) towards test target 12 according to a planned test pattern to yield an actual test pattern on test target 12. Examples of auxiliary light system 26 are described in more detail with reference to FIGS. 3A to 3C.

Figure 2:
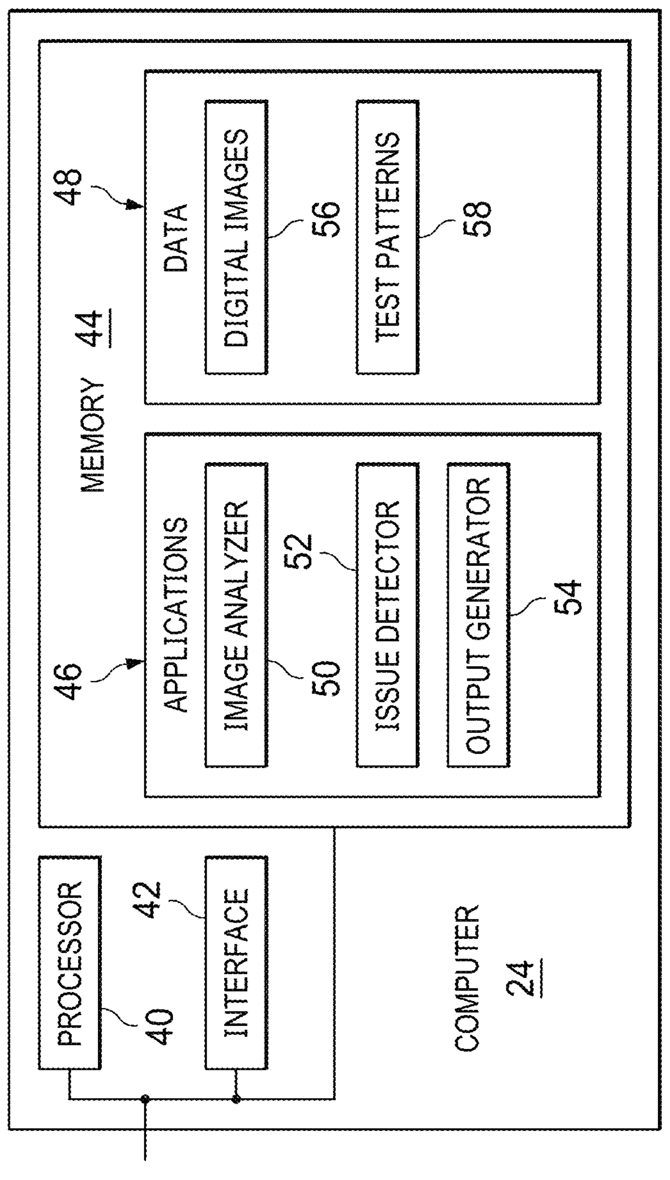
FIG. 2 illustrates an example of the computer of the system of FIG. 1, according to certain embodiments.

FIG. 2 illustrates an example of computer 24 of system 10 of FIG. 1, according to certain embodiments. In the example, computer 24 includes processor 40, interface 42, and memory 44, which stores applications 46 and data 48. Applications 46 include an image analyzer 50, issue detector 52, and output generator 54. Data 48 include digital images 56 and test patterns 58.

Digital Images. Digital images 56 include digital images of actual test patterns generated by imaging system 22 at any suitable time, e.g., within the current minute, hour, day, week, month, or one or more years. Computer 24 may analyze a recently generated image in order to immediately detect a problem or may analyze images generated within a longer time period to detect trends that occurred during the period. Digital images 56 may also include digital images of calibration patterns used to calibrate system 10, examples of which are described in more detail with reference to FIGS. 12A and 12B. In certain cases, a digital image may be a composite of multiple images taken from different cameras and/or taken at different times.

Test Patterns. A planned test pattern instructs laser system 20 to direct a laser beam and/or auxiliary light system 26 to direct an auxiliary beam towards one or more particular locations according to a specific pattern. The resulting one or more irradiated locations (e.g., laser and/or auxiliary spots) constitute the actual test pattern. A planned irradiated location of the planned test pattern yields a corresponding actual irradiated location of the actual test pattern, e.g., a planned spot yields a corresponding actual spot when the laser beam and/or the auxiliary beam is actually directed to the test target 12. Examples of test patterns are described in more detail with reference to FIGS. 4A to 12B.

Image Analysis. Image analyzer 50 uses image processing to analyze digital images. In certain embodiments, analyzer 50 uses grayscale analysis. The grayscale value of a pixel represents the brightness or intensity value of the pixel and may be expressed in any suitable manner, such as 0 or 0% for total absence, black, and 1 or 100% for total presence, white. In the embodiments, analyzer 50 determines the grayscale values of the pixels of a digital image of an actual test pattern. Analyzer 50 then identifies a subset of the grayscale values that represent actual laser and/or auxiliary spots of the test pattern, e.g., lighter or white values. For example, grayscale values of an irradiated color represent an actual spot. In some cases, grayscale values can indicate the degree of irradiation, such that some values indicate more irradiation and other values indicate less radiation. The pixels with grayscale values that represents actual spots indicate the locations of the spots such that analyzer 50 can ascertain the actual test pattern. Although this example uses grayscale analysis, any suitable analysis may be used, e.g., a color analysis that utilizes chromatic colors. Accordingly, "grayscale" values may refer to chromatic values generally.

In certain embodiments, analyzer 50 calculates the length of a dimension (e.g., a separation between laser spots or a diameter of a laser spot) in an actual test pattern using a mathematical relationship between length and pixels of the digital image. For example, the mathematical relationship may be p pixels are equal to q units of length, which may be expressed as a ratio p/q or q/p. In the embodiments, analyzer 50 determines the number of pixels that the dimension covers and uses the relationship to translate the number of pixels to length units. In certain embodiments, analyzer 50 can perform a calibration process to determine the mathematical relationship between length and pixels. An example of determining a relationship is described below with reference to FIG. 14.

In certain embodiments, analyzer 50 can detect trends in multiple test patterns produced over time. In the embodiments, analyzer 50 accesses and analyzes previous actual test patterns taken over, e.g., a number of weeks, months, or years, to detect a trend of a previous issue with the laser system. For example, analyzer 50 may detect that scanner 32 tends to become misaligned after a certain number of procedures. Analyzer 50 may provide an output that notifies the user of potential misalignment during a warning period prior to the performance of the number of procedures.

Issue Detection. Issue detector 52 compares the actual test pattern to the planned test pattern, detects deviations of the actual from the planned test pattern, and identifies issues indicated by the deviations. A deviation may be a difference greater than a predetermined margin of error, e.g., 2, 5, or 10 percent. In certain embodiments, the planned and/or actual test patterns are converted to the same or similar formats so issue detector 52 can compare the test patterns. For example, the planned test pattern may describe spot locations. As described above, the grayscale values that represent actual spots indicate the locations of the spots, so the actual test pattern may also describe spot locations.

Output Generation. Output generator 54 generates and provides output in response to the identified issues. Any suitable output may be provided. Examples of output may include one or more of the following. In certain situations, the output may be a warning that notifies a user of a problem with the system. For example, system 10 may display a notification or warning information (e.g., text, photo, or graph), display an error message, or provide an audio or visual warning.

In certain situations, the output may be a command sent to laser system 20 that addresses the problem. For example, the command may include instructions to adjust beam scanner 32 to correct a detected problem, prevent laser system 20 from generating a laser beam, or shut off laser system 20. In certain embodiments, output generator 54 can calculate a correction to remove the deviation and generate a command to instruct the scanner to implement the correction. For example, output generator 54 may determine scanner 32 is guiding the laser beam with a distance error and generate a command that adjusts scanner 32 to remove the distance error. In an example, the distance error in pixels $x_{err}=+x$, so the correction in pixels may include $x_{corr}=-x$. Output generator 54 can use a mathematical relationship between length and pixels, such as p pixels are equal to q units of length, to convert the correction in pixels to the correction in length units to generate a command scanner 32 can use. In the example, the correction in length $x'_{corr}$=correction in pixels $x_{corr}\times$(q length units/p pixels)=$-x\times(q/p)$.

In certain situations, the output may report information about the long-term performance of system 10. For example, the report may describe the history of previous actual laser pattern analysis, describe a trend of an issue, or warn of a predicted issue, which may be provided to a service technician, the laser manufacturer, or a regulatory organization.

Figure 3A:
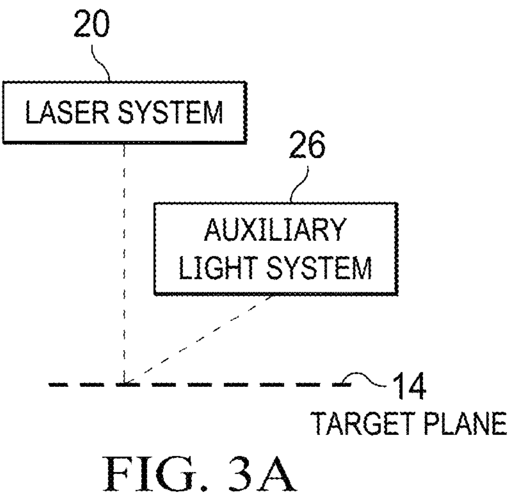
FIGS. 3A to 3C illustrate examples of auxiliary light systems that may be included in the system of FIG. 1, according to certain embodiments.
Figure 3B:
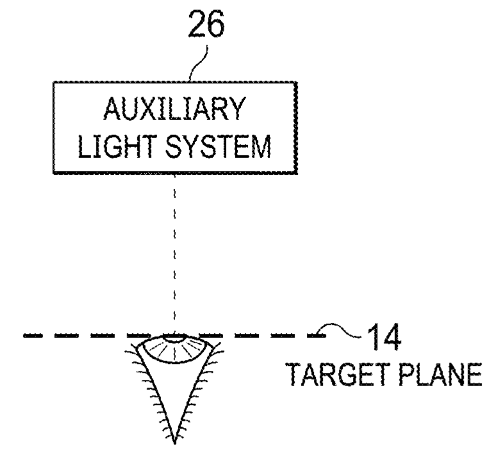
Figure 3C:
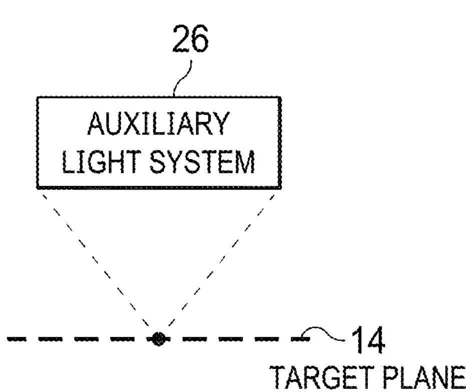

FIGS. 3A to 3C illustrate examples of auxiliary light systems 26 that may be included in system 10 of FIG. 1, according to certain embodiments. Auxiliary light system 26 directs auxiliary light (e.g., a laser beam or illumination light) towards test target 12 according to a planned test pattern of planned auxiliary spots. The planned test pattern yields an actual test pattern of actual auxiliary spots on test target 12. Examples of auxiliary light include an aiming beam, fixation light, illumination light, and distance beams.

FIG. 3A illustrates an example of auxiliary light system 26 that generates an aiming beam that indicates the location of a laser spot, such as a treatment laser spot, formed by laser system 20. In the embodiments, auxiliary light system 26 directs the aiming beam to yield an aiming spot at a predetermined location relative to a planned treatment laser spot. The predetermined location may be, e.g., at or adjacent to the planned treatment laser spot. In an example, the aiming spot may be formed prior to formation of the treatment laser spot to indicate the location that the actual treatment laser spot will be. In another example, the aiming spot may be formed after the formation of the treatment laser spot to indicate the location of the actual treatment laser spot.

FIG. 3B illustrates an example of auxiliary light system 26 that directs the auxiliary light to any suitable predetermined coordinates of the xyz-coordinate system, such as xy-coordinates of the xy-plane located at the treatment plane. In the illustrated example, the auxiliary light is a fixation light on which the patient is to fixate their gaze. Auxiliary light system 26 directs the fixation light to xy-coordinates where the patient is to fixate their gaze. As another example, the auxiliary light is illumination light that illuminates the surgical site. Auxiliary light system 26 directs the fixation light to the xy-coordinates of the surgical site.

FIG. 3C illustrates an example of auxiliary light system 26 that creates distance beams that indicate distance in the z-direction. In the example, auxiliary light system 26 includes laser diodes arranged at an angle to yield beams that intersect at target plane 14. When target plane 14 is at the correct z-position, the laser spots formed by the beams overlap.

Figure 4A:
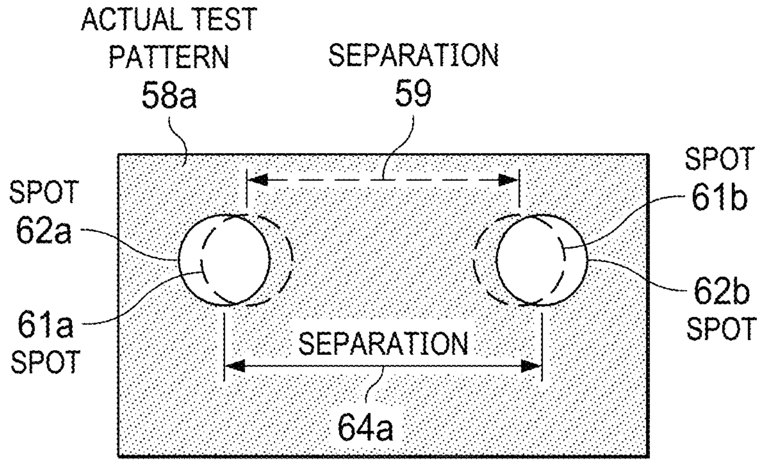
FIGS. 4A and 4B illustrate an example of detecting spot separation that may be performed by the system of FIG. 1, according to certain embodiments.
Figure 4B:
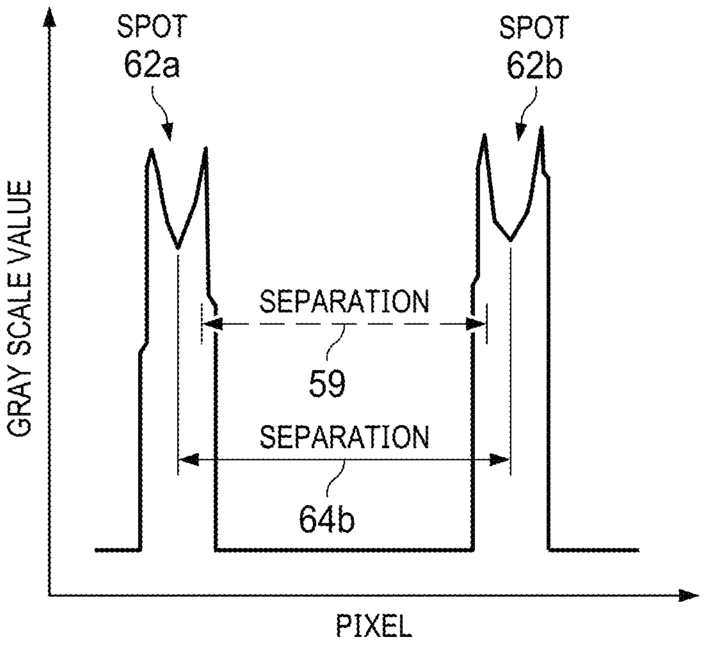

FIGS. 4A and 4B illustrate an example of detecting spot separation that may be performed by system 10 of FIG. 1, according to certain embodiments. In the example, the planned test pattern has a first planned laser spot 61*a* at a predetermined spot separation (i.e., distance) 59 from a second planned laser spot 61*b*. The planned test pattern yields an actual test pattern 58*a* on test target 12 located at target plane 14. Actual test pattern 58*a* has corresponding actual laser spots 62*a-b* with an actual spot separation 64*a* (e.g., distance in length). Imaging system 22 captures a digital image of actual test pattern 58*a*.

In the example, analyzer 50 determines grayscale values of the pixels of the digital image and identifies the subset of grayscale values that represent laser spots 62*a-b*. Analyzer 50 then determines actual separation 64*b* (e.g., distance in pixels) between laser spots 62*a-b*. Analyzer 50 may translate actual separation 64*b* given in pixels to actual separation 64*a* given in length using a mathematical relationship between length and pixels. Issue detector 52 detects a deviation of the actual spot separation 64*a* from the planned spot separation 59. This deviation may indicate that the scanner cannot properly guide the laser beam to yield the predetermined spot separation.

Figure 5A:
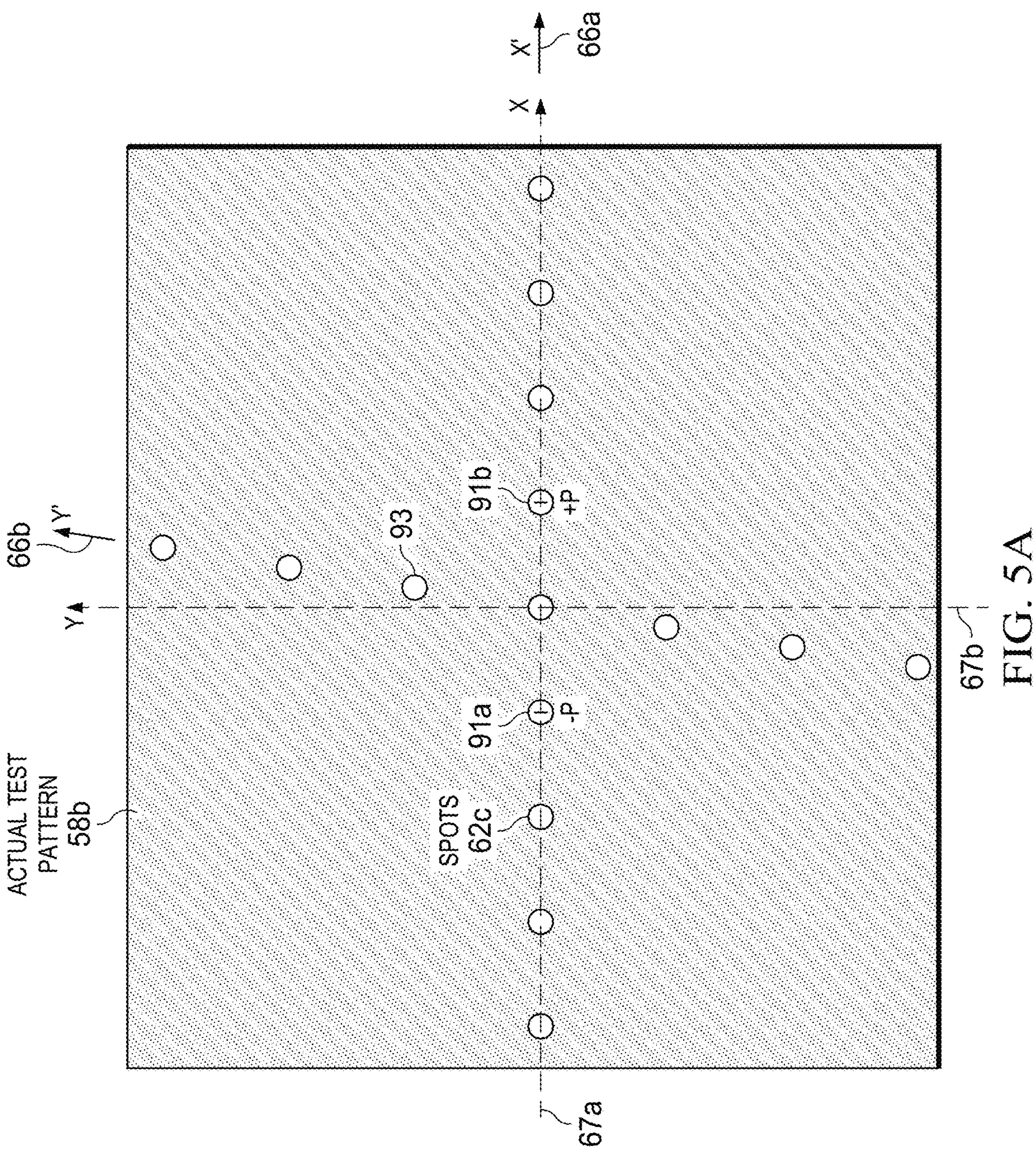
FIGS. 5A through 5C illustrate an example of detecting the orthogonality of axes of an actual laser pattern that may be performed by the system of FIG. 1, according to certain embodiments.
Figure 5B:
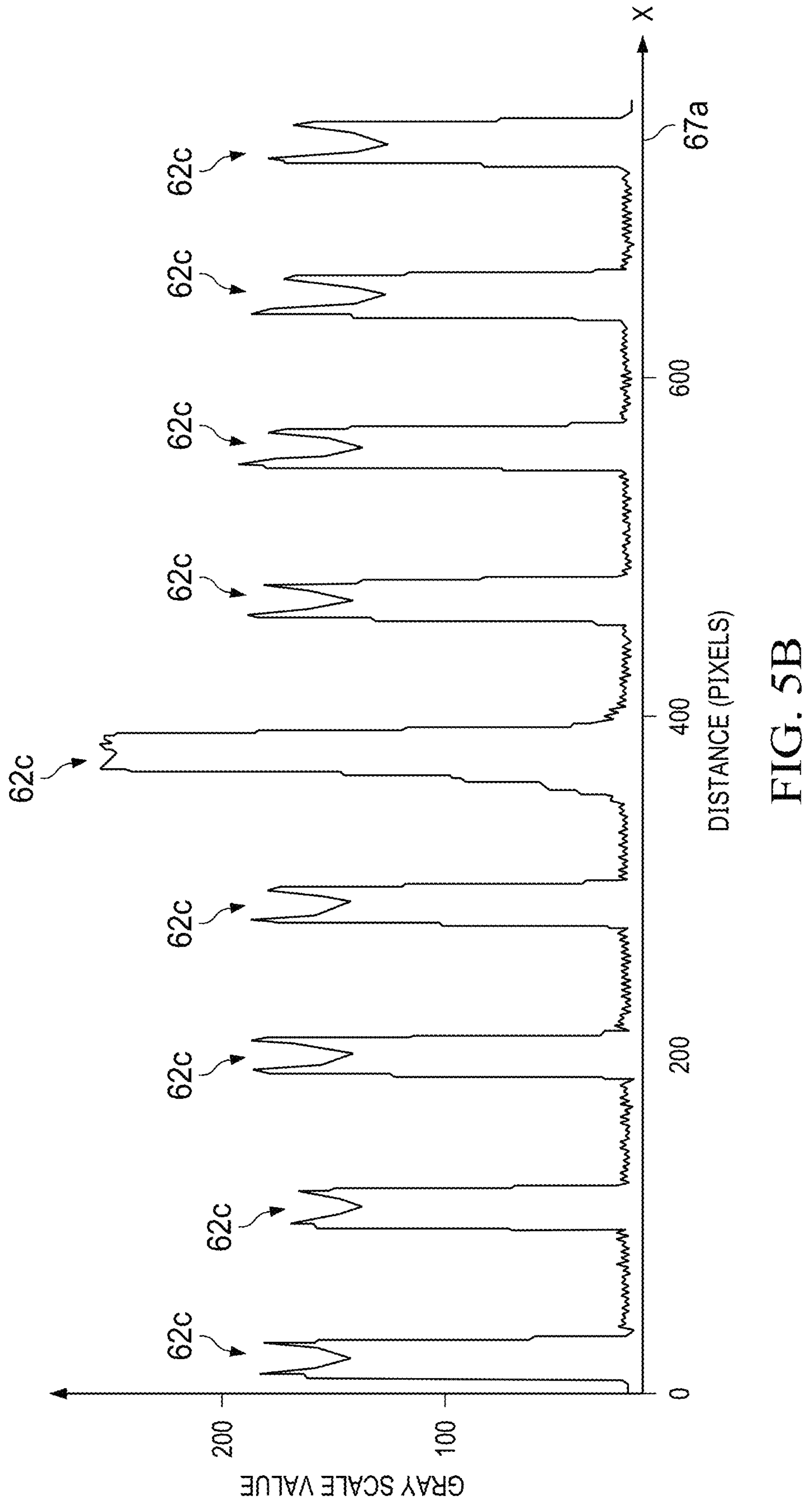
Figure 5C:
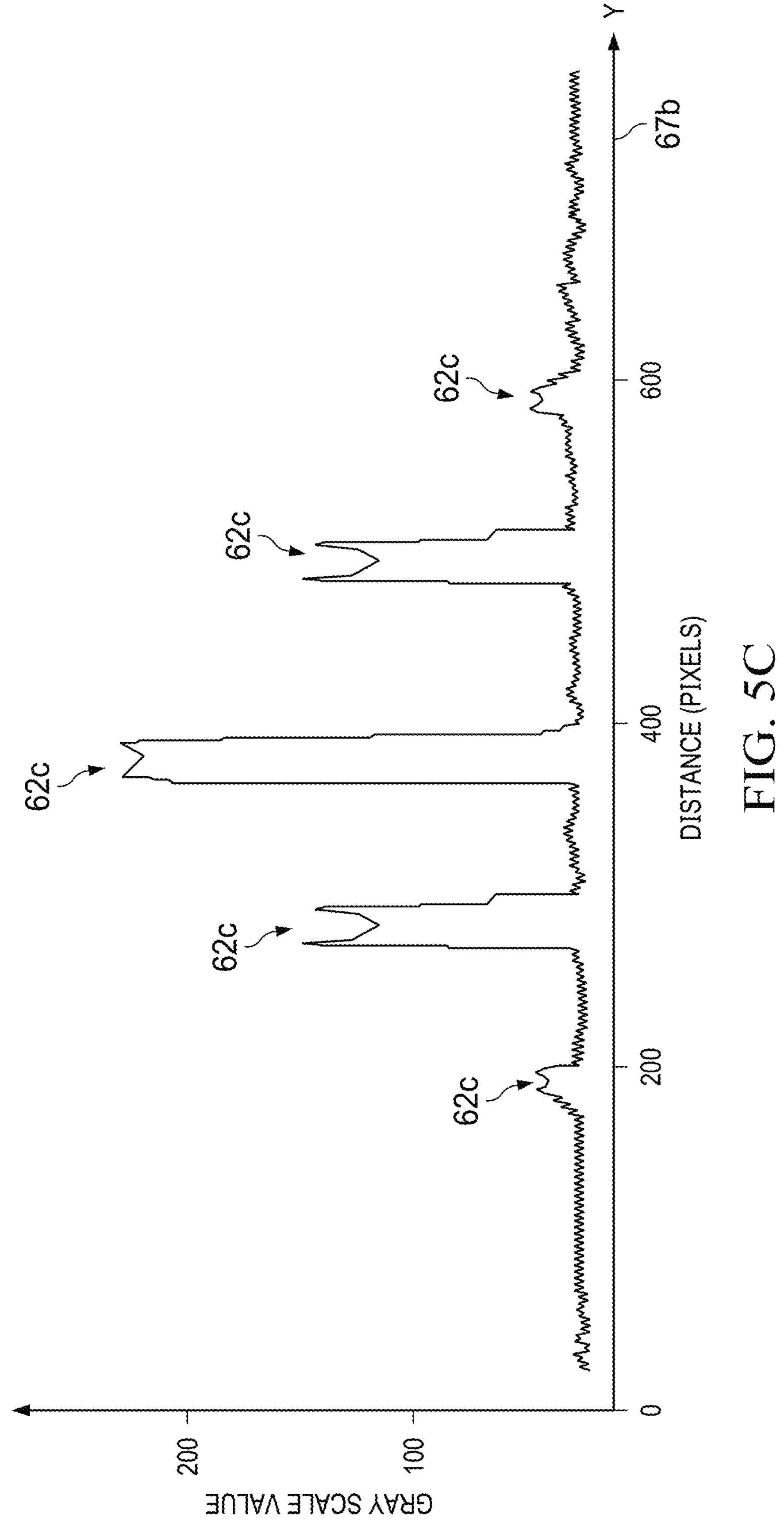

FIGS. 5A through 5C illustrate an example of detecting the orthogonality of the axes of an actual laser pattern that may be performed by system 10 of FIG. 1, according to certain embodiments. In the example, the planned test pattern has laser spots along a first planned axis orthogonal to a second planned axis, e.g., the planned test pattern instructs laser system 20 to form laser spots along a planned x-axis 67*a* and a planned y-axis 67*b* of the coordinate system of laser system 20. The planned test pattern yields actual test pattern 58*b* on test target 12. Actual test pattern 58*b* has actual laser spots 62*c* along a first actual axis, the actual x'-axis 66*a*, and a second actual axis, the actual y'-axis 66*b*. Imaging system 22 captures a digital image of actual test pattern 58*b*.

Analyzer 50 determines grayscale values of the pixels of the digital image and identifies the subset of grayscale values that represent actual laser spots 62*c*. Analyzer 50 may then use any suitable manner to determine whether the actual x'- and y'-axes 66*a-b* are orthogonal. In certain examples, grayscale values along the planned x-axis 67*a* (FIG. 5B) and planned y-axis 67*b* (FIG. 5C) are analyzed. Along the planned x-axis 67*a*, actual laser spots 62*c* of the x'-axis 66*a* appear, indicating that the actual laser spots 62*c* are aligned with the planned x-axis 67*a*. However, along the planned y-axis 67*b*, the actual laser spots 62*c* of the y'-axis

66*a* that are farther from the center either barely appear or do not appear at all, indicating that the actual laser spots 62*c* are not aligned with the planned y-axis 67.

In other examples, analyzer 50 first identifies the actual x'- and y'-axes 66*a-b* from the grayscale values that represent the actual laser spots. Analyzer 50 then determines the orthogonality of the actual x'- and y'-axes 66*a-b* in any suitable manner. For example, analyzer 50 identifies actual spots 91*a* and 91*b* that are located at −p and +p units, respectively, of the actual x'-axis 66*a* and identifies actual spot 93 that is located on the actual y'-axis 66*b*. Analyzer 50 measures the distances between spots 91*a* and 93 and between spots 93 and 91*b*. The distances should be equal, but in the illustrated example the distance between spots 91*a* and 93 is greater than the distance between spots 93 and 91*b*, indicating the actual x'- and y'-axes 66*a-b* are not orthogonal. A deviation in orthogonality may indicate that the scanner is misaligned or that the laser beam and the target plane are misaligned.

Figure 6:
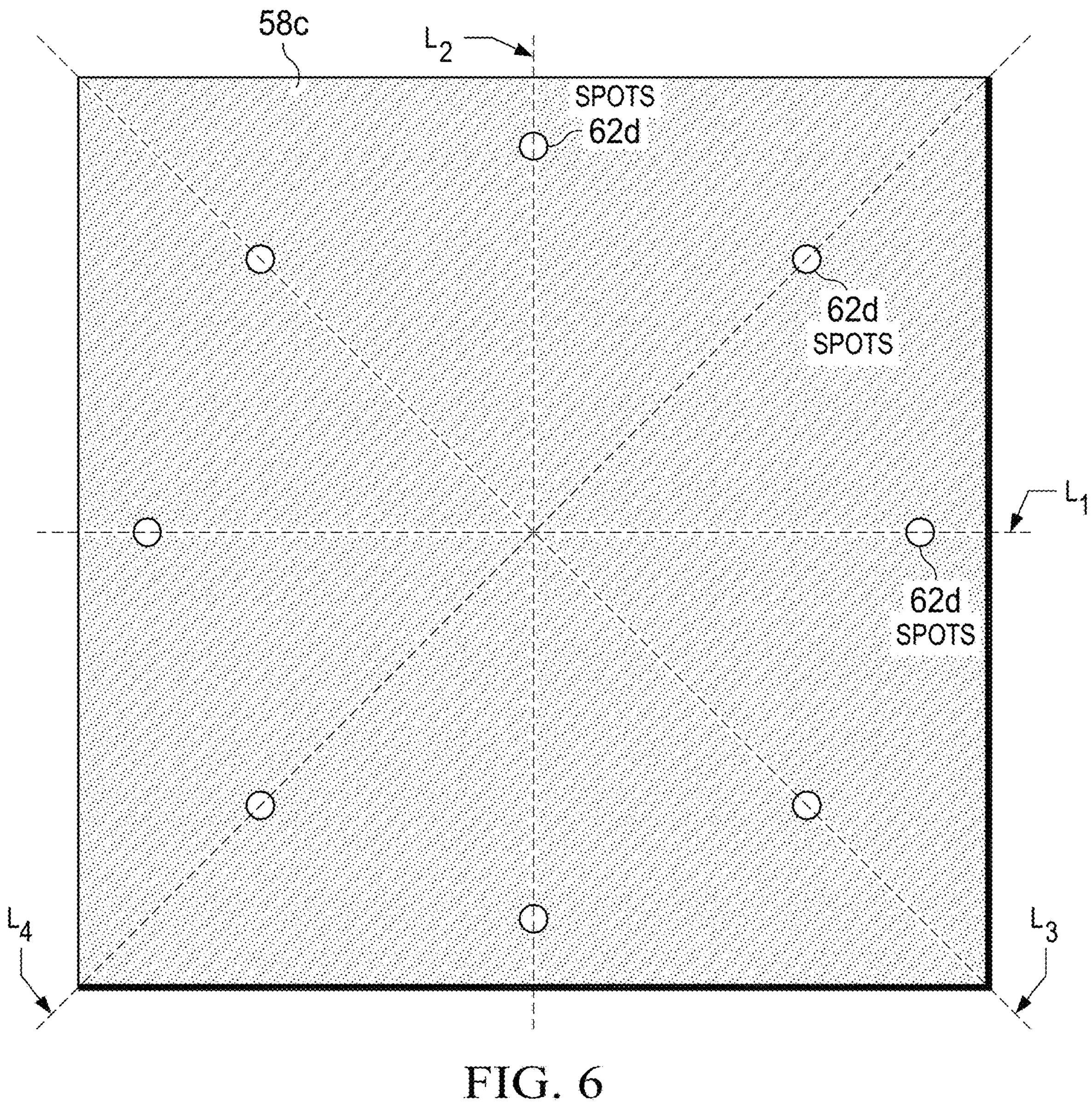
FIG. 6 illustrates an example of detecting the geometric shape of an actual laser pattern that may be performed by the system of FIG. 1, according to certain embodiments.

FIG. 6 illustrates an example of detecting the geometric shape of an actual laser pattern that may be performed by system 10 of FIG. 1, according to certain embodiments. The planned test pattern may have any suitable geometric shape, e.g., an oval (circular or non-circular); a polygon (regular or irregular) of any suitable number of sides, such as a rectangle or square; or an array (one or two-dimensional). In the illustrated example, the shape is a circle, and planned test pattern yields actual test pattern 58*c* on test target 12. Actual test pattern 58*c* has actual laser spots 62*d* that outline the geometric shape. Imaging system 22 captures a digital image of actual test pattern 58*c*.

In the example, analyzer 50 determines grayscale values of the pixels of the digital image and identifies the subset of grayscale values that represent actual laser spots 62*d*. Analyzer 50 can use techniques described herein to determine if the actual shape matches the planned shape. For example, analyzer 50 can examine the grayscale values of the laser spots 62*d* along lines L1 through L4. The spot separation of spots 62*d* along a line L can be checked using the technique described in FIGS. 4A and 4B, and the orthogonality of lines L1 and L2 and of lines L3 and L4 can be checked using the technique described in FIG. 5A to 5C. In these and other embodiments, issue detector 52 may detect a deviation of the actual from the planned test pattern when the geometric shape of the actual test pattern is not the same as the geometric shape of the planned test pattern. This deviation may indicate that the scanner is misaligned or that the laser beam and the target plane are misaligned.

Figure 7A:
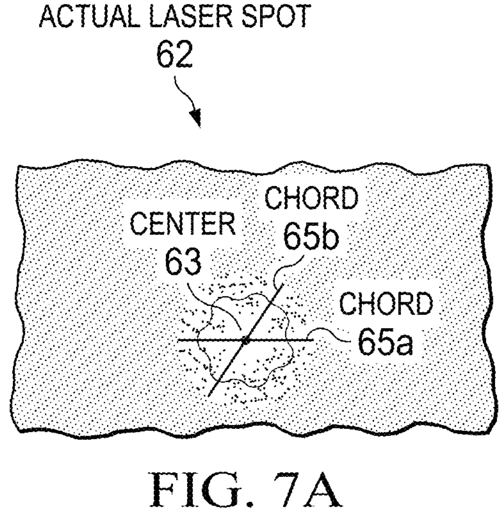
FIGS. 7A and 7B illustrate an example of detecting laser beam features that may be performed by system 10 of FIG. 1, according to certain embodiments.
Figure 7B:
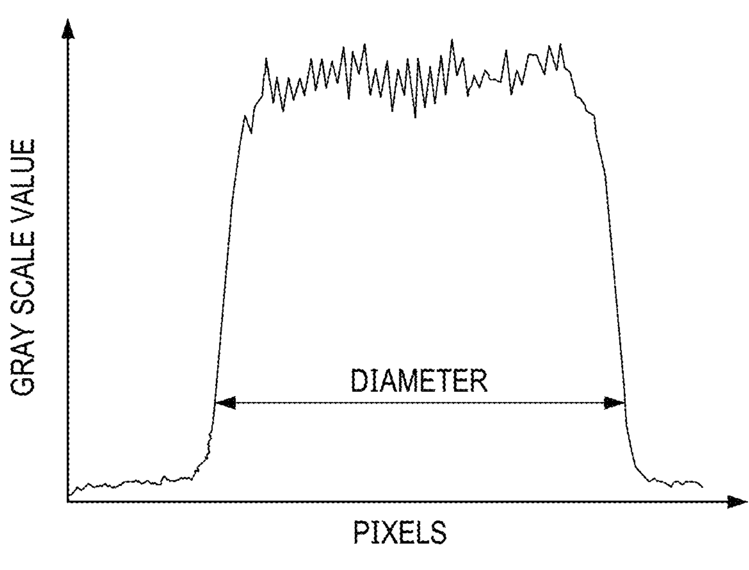

FIGS. 7A and 7B illustrate an example of detecting laser beam features that may be performed by system 10 of FIG. 1, according to certain embodiments. Laser beam features may include, e.g., the diameter and/or cross-section shape of a laser beam. The digital image of an actual laser spot 62 can be analyzed to determine laser beam features. For example, the diameter of actual laser spot 62 indicates the beam diameter, and the shape of actual laser spot 62 indicates the cross-section shape.

In the illustrated example, a planned laser spot has planned beam features, e.g., a planned diameter and/or shape. Imaging system 22 captures a digital image of actual laser spot 62. Analyzer 50 determines grayscale values of the pixels of the digital image and identifies the subset of grayscale values that represent laser spot 62. Analyzer 50 then determines the actual beam features using the digital image, as described in the examples below. Analyzer 50 may translate a beam feature given in pixels of the image to the feature given in length using a mathematical relationship between length and pixels. Issue detector 52 detects a deviation of actual from planned beam features. A deviation may be a difference greater than a predetermined margin of error, e.g., 2, 5, or 10 percent. The deviation may indicate that, e.g., a beam control device cannot properly control the laser beam to yield the planned beam feature or that the laser beam is not properly aligned with the target plane. Computer 24 may provide instructions to adjust the beam control device or to align the laser beam with the target plane to yield the planned beam features.

Analyzer 50 may determine actual beam features in any suitable manner. For example, analyzer 50 determines the diameter of laser spot 62 by measuring a chord 65 (65*a* or 65*b*) that intersects the center 63 of spot 62 (a "diameter chord"). As another example, analyzer 50 determines the shape of laser spot 62 by measuring two or more diameter chords 65*a-b* that intersect center 63 of spot 62. In some cases, a pair of the chords 65 may be orthogonal. If the length of the chords 65 are substantially the same, analyzer 50 determines that the shape is circular. Otherwise, analyzer 50 determines that the shape is not circular, such as a non-circular ellipse. If the shape is elliptical, analyzer 50 may determine the lengths and/or directions of the longest and/or shortest chords 65. The lengths and/or directions may be given in, e.g., the xy-plane at z=0 or an xyz-direction of the xyz-coordinate system.

Computer 24 may provide instructions to adjust the beam control device or to align the laser beam with the target plane in any suitable manner. For example, computer 24 may identify a beam control device (e.g., a lens) responsible for the beam diameter or cross section shape and instruct the beam control device to adjust the focal length and/or beam divergence/convergence to yield the planned beam diameter or cross-section shape. As another example, computer 24 may identify a component of laser system 20 (e.g., scanner 32 or target platform 16) responsible for the alignment of the laser beam relative to target plane 14 and instruct the component to align the laser beam and target plane to yield the planned cross-section shape.

Figure 8A:
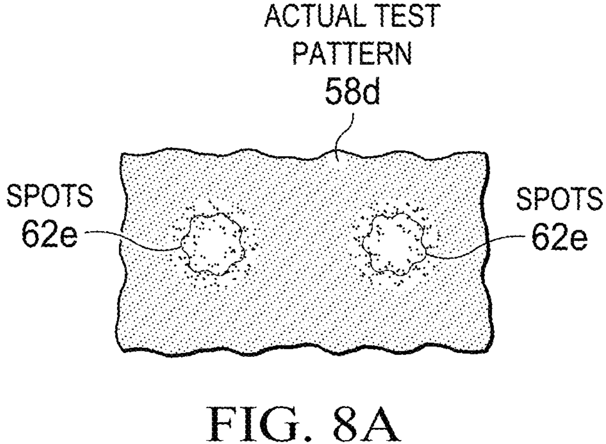
FIGS. 8A and 8B illustrate an example of detecting blurry laser spots that may be performed by the system of FIG. 1, according to certain embodiments.
Figure 8B:
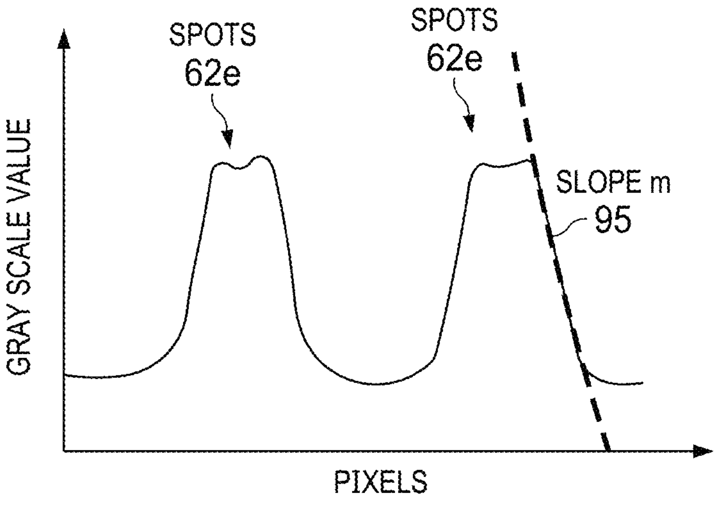

FIGS. 8A and 8B illustrate an example of detecting blurry laser spots that may be performed by system 10 of FIG. 1, according to certain embodiments. In the example, the border of a planned laser spot has a planned sharpness, which may be described in any suitable manner. In certain embodiments, the sharpness may be described as a relationship between the grayscale values and pixel location, where a faster transition between pixels that represent laser spots and pixels that do not represent laser spots indicate a sharper border. In the illustrated example, sharpness may be represented by slope m 95 that measures the change in grayscale value $\Delta g$ over the change in number of pixels $\Delta p$ that occurs between pixels that represent laser spots 62*e* and pixels that do not. In the example, a threshold slope M represents the minimum acceptable sharpness for laser spots. A threshold slope may be calculated from digital images of acceptable laser spots, identified by a user, or determined by any other suitable approach. In these and other embodiments, a slope $m<M$ may indicate that laser spots 62*e* have less than acceptable sharpness.

To detect blurry laser spots, the test pattern may have one, two, or more laser spots. In the illustrated example, imaging system 22 captures a digital image of actual test pattern 58*d* with laser spots 62*e*. Analyzer 50 determines grayscale values of the pixels of the digital image and identifies the subset of grayscale values that represent actual laser spots 62*e*. Issue detector 52 detects that laser spots 62*e* are blurrier than expected. For example, issue detector 52 calculates the slope m<M that indicates that laser spots 62*e* have less than acceptable sharpness. This deviation may indicate that system 20 is experiencing an unwanted vibration or a beam control device cannot properly focus the laser beam.

FIGS. 9A to 11B illustrate examples of detecting the alignment of auxiliary light of auxiliary light system 26 that may be performed by system 10 of FIG. 1, according to certain embodiments. Auxiliary light system 26 directs auxiliary light (e.g., a laser beam or illumination light) towards test target 12 according to a planned test pattern of one or more planned auxiliary spots. The planned test pattern yields an actual test pattern of one or more actual auxiliary spots on test target 12. Examples of auxiliary light include aiming beams, fixation light, illumination light, and distance beams.

Figure 9A:
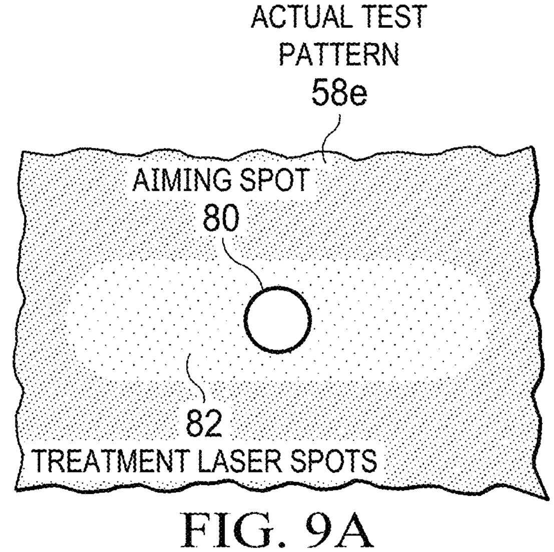
FIGS. 9A and 9B illustrate an example of detecting aiming beam alignment that may be performed by system 10 of FIG. 1, according to certain embodiments.
Figure 9B:
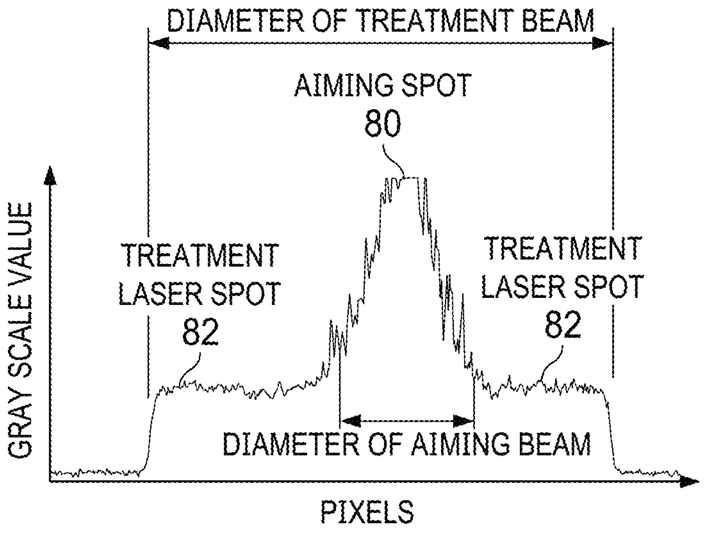

FIGS. 9A and 9B illustrate an example of detecting aiming beam alignment that may be performed by system 10 of FIG. 1, according to certain embodiments. In the example, the planned test pattern has a planned aiming spot that is centered about or within a line of planned treatment laser spots formed by laser system 20. The planned test pattern yields an actual test pattern 58*e* that includes an actual aiming spot 80 and actual treatment laser spots 82. Imaging system 22 captures a digital image of actual test pattern 58*e*.

In the example, analyzer 50 determines grayscale values of the pixels of the digital image and identifies the subset of grayscale values that represent actual aiming spot 80 and treatment laser spots 82. Analyzer 50 determines the relative locations of spots 80 and 82, and issue detector 52 detects whether actual aiming spot 80 is centered about or within actual treatment laser spots 82. Issue detector 52 may also determine the length and/or direction of the deviation of actual aiming spot 80 from the planned aiming spot. For example, if the planned aiming spot is supposed to be at the same location as the central laser spot 82 in the line of spots 82, issue detector 52 may determine the length and/or direction of the deviation between actual aiming spot 80 and the laser spot 82. If the aiming beam is not properly aligned, computer 24 instructs auxiliary light system 26 to adjust the aiming beam to align the beam. Computer 24 may instruct auxiliary light system 26 to move the aiming beam in the opposite length and/or direction of the deviation to remove the deviation.

Figure 10A:
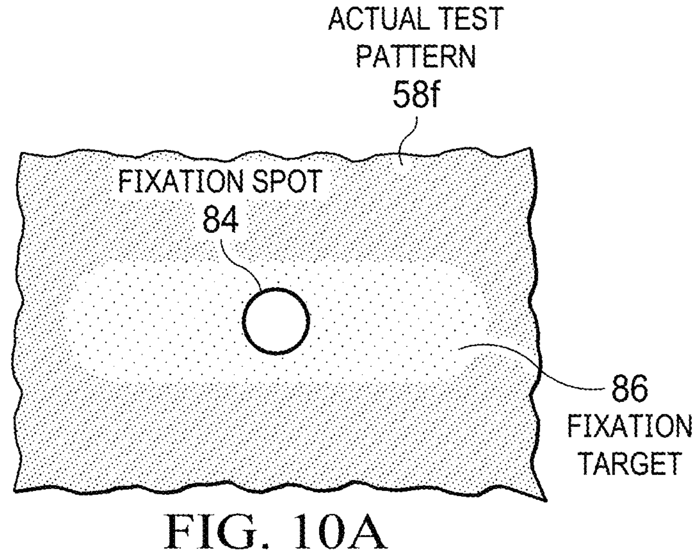
FIGS. 10A and 10B illustrate an example of detecting fixation light alignment that may be performed by system 10 of FIG. 1, according to certain embodiments.
Figure 10B:
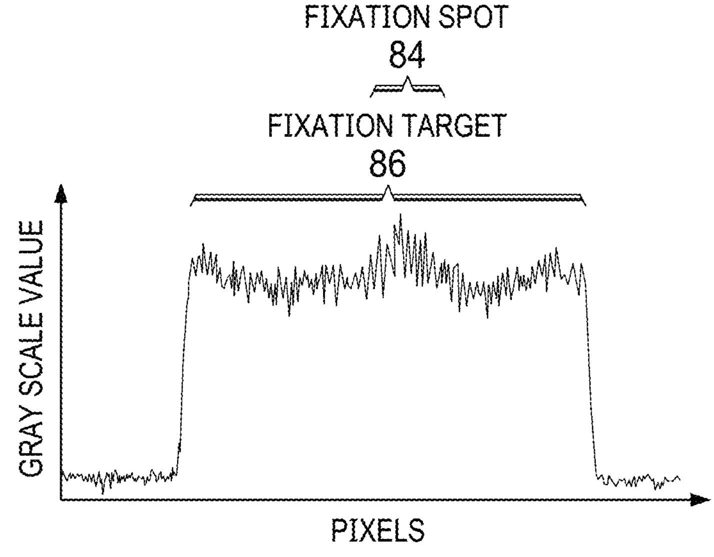

FIGS. 10A and 10B illustrate an example of detecting fixation light alignment that may be performed by system 10 of FIG. 1, according to certain embodiments. In the example, the planned test pattern has a planned fixation spot centered within a planned fixation target that represents (x, y) coordinates where the patient is to fixate their gaze, e.g., where the treatment beam will be located, such as the (0, 0) point of the laser coordinate system. In the example, fixation target 86 is a row of laser spots created with the laser beam of laser system 20. The planned test pattern yields an actual test pattern 58*f* with an actual fixation spot 84 relative to fixation target 86 at target plane 14. Imaging system 22 captures a digital image of actual test pattern 58*f*.

In the example, analyzer 50 determines grayscale values of the pixels of the digital image and identifies the subset of grayscale values that represent actual fixation spot 84 relative to fixation target 86. Analyzer 50 determines the relative locations of spot 84 and target 86, and issue detector 52 detects whether actual fixation spot 84 is centered within fixation target 86. Issue detector 52 may also determine the length and direction of the deviation of actual fixation spot 84 from planned fixation spot 84. If the fixation beam is not properly aligned, computer 24 instructs auxiliary light system 26 to adjust the fixation beam to align the beam. Computer 24 may instruct auxiliary light system 26 to move the fixation beam in the opposite length and direction of the deviation to remove the deviation.

FIGS. 11A through 11D illustrate an example of detecting distance beam alignment that may be performed by system 10 of FIG. 1, according to certain embodiments. In the example, the planned test pattern has planned distance spots that overlap at target plane 14. The planned test pattern yields an actual test pattern 58*g* with actual distance spots 88 at target plane 14. Imaging system 22 captures a digital image of actual test pattern 58*g*.

Figure 11A:
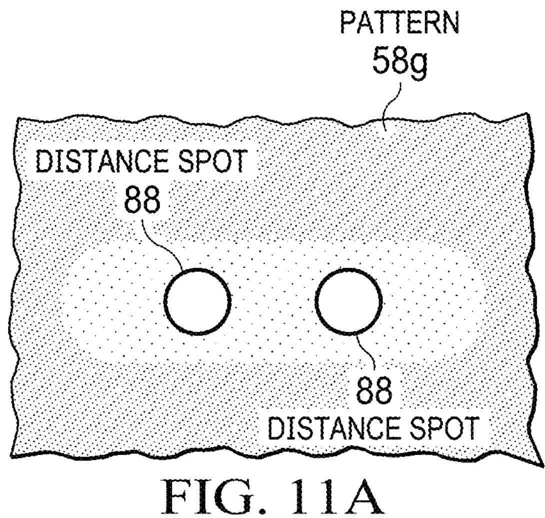
FIGS. 11A through 11D illustrate an example of detecting distance beam alignment that may be performed by system 10 of FIG. 1, according to certain embodiments.
Figure 11B:
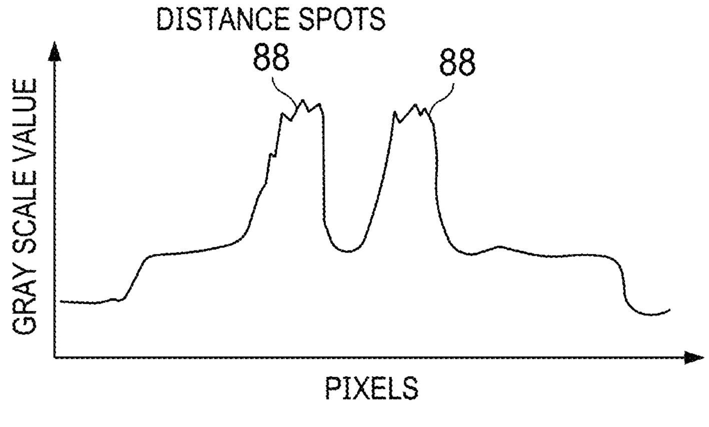
Figure 11C:
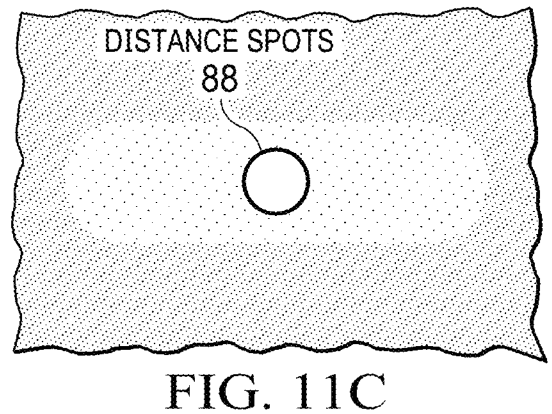
Figure 11D:
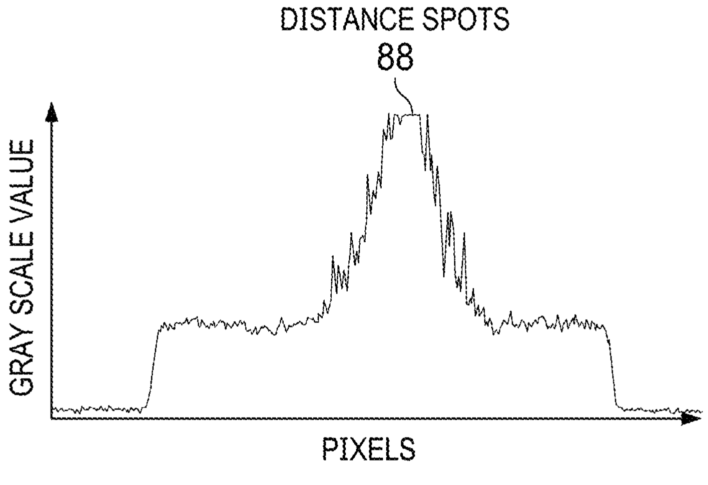

In the example, analyzer 50 determines grayscale values of the pixels of the digital image and identifies the subset of grayscale values that represent actual distance spots 88. Analyzer 50 determines the relative locations of distance spots 88, and issue detector 52 detects whether distance spots 88 overlap. In the example of FIGS. 11A and 11B, the actual distance spots 88 do not overlap, indicating the distance beams are not properly aligned. Issue detector 52 may also determine the length of the separation of actual distance spots 88. Computer 24 may instruct auxiliary light system 26 to adjust the distance beams to align the beams. For example, computer 24 may instruct auxiliary light system 26 to move the distance beams closer together to yield actual distance spots 88 that move together by the separation length to remove the separation. In the example of FIGS. 11C and 11D, the actual distance spots 88 overlap, indicating the distance beams are properly aligned.

Figure 12A:
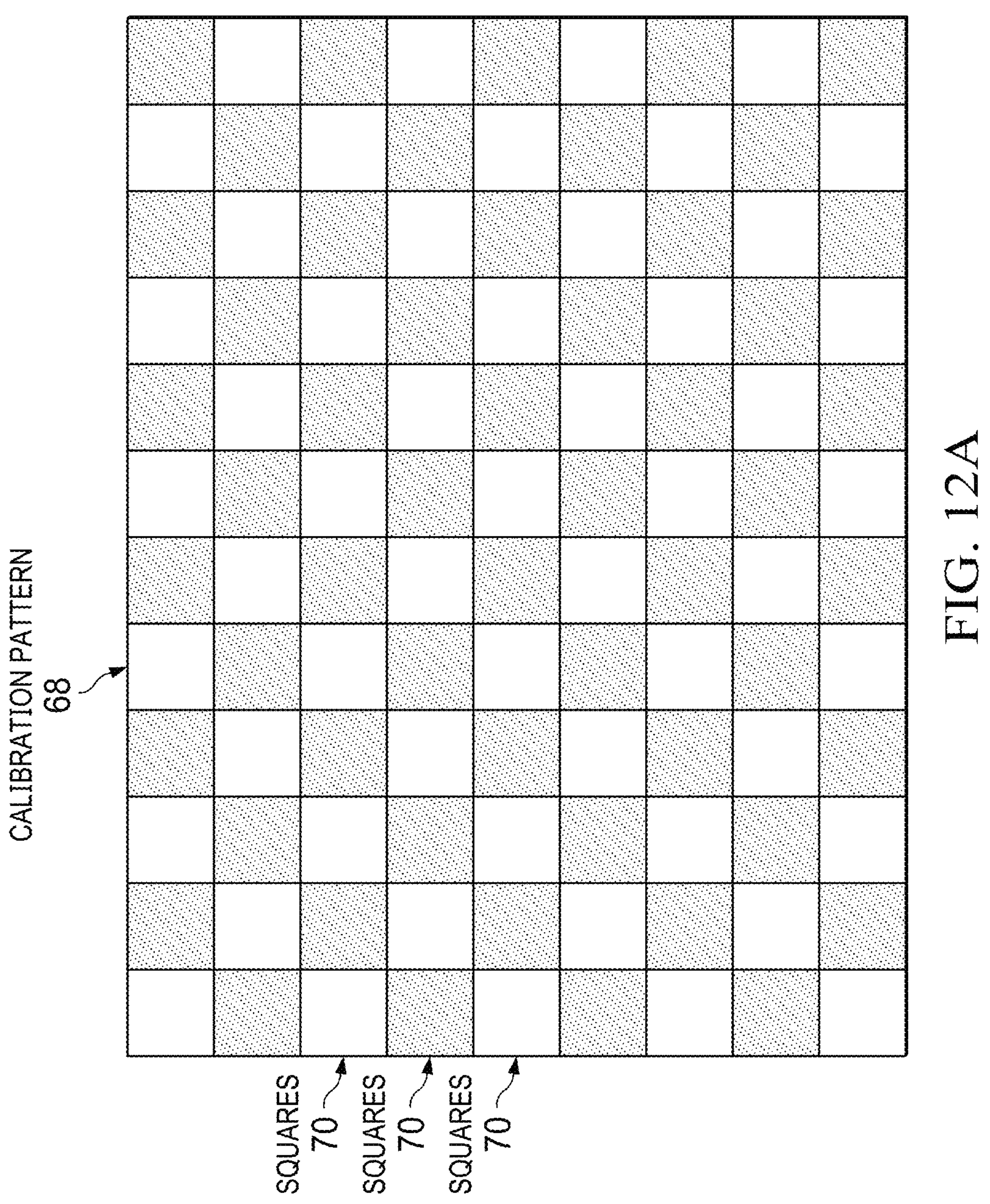
FIGS. 12A and 12B illustrate an example of using a calibration pattern to determine a mathematical relationship between length and pixels that may be performed by the system of FIG. 1, according to certain embodiments.
Figure 12B:
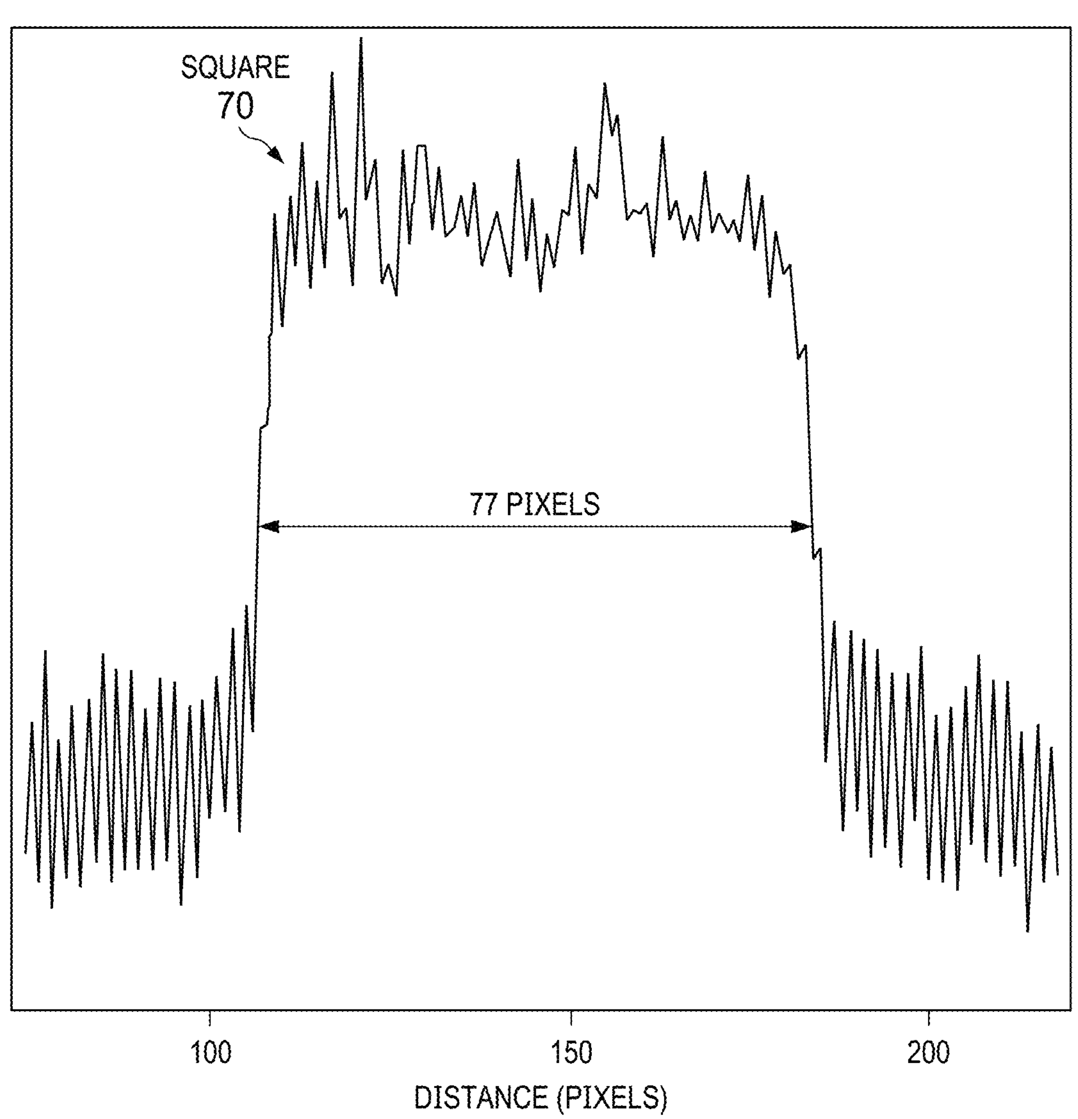

FIGS. 12A and 12B illustrate an example of using a calibration pattern 68 to determine a mathematical relationship between length and pixels that may be performed by system 10 of FIG. 1, according to certain embodiments. In general, a calibration pattern shows a known length, e.g., a length in the range of 0.5 to 2, 2 to 5, 5 to 10, 10 to 20, 20 to 50, and/or 50 or more millimeters (mm), such as 1 mm. The calibration pattern may be, e.g., a line with segments of the known length or a grid (e.g., a chessboard pattern) with squares having sides of the known length. In the illustrated example, calibration pattern 68 is a chessboard pattern with squares having sides of 1 mm.

In certain embodiments, analyzer 50 uses calibration pattern 68 to determine a mathematical relationship between length and pixels of a digital image generated by system 10. In the illustrated example, imaging system 22 captures a digital calibration image of calibration pattern 68 located at target plane 14. Analyzer 50 determines grayscale values of the pixels of the digital image (e.g., calibration grayscale values) and then identifies the subset of grayscale values that represent the known lengths, e.g., the squares. Analyzer 50 then determines the number of pixels that correspond to the known length, e.g., the number of pixels across which the known length extends. Any suitable number of pixels may correspond to the known length, depending on, e.g., the pixel resolution and distance between imaging system 22 and test target 12, such as 50 to 100, 100 to 250, and 250 to 500 pixels. In the example, 77 pixels correspond to one square, so 77 pixels correspond to 1 mm.

Figure 13:
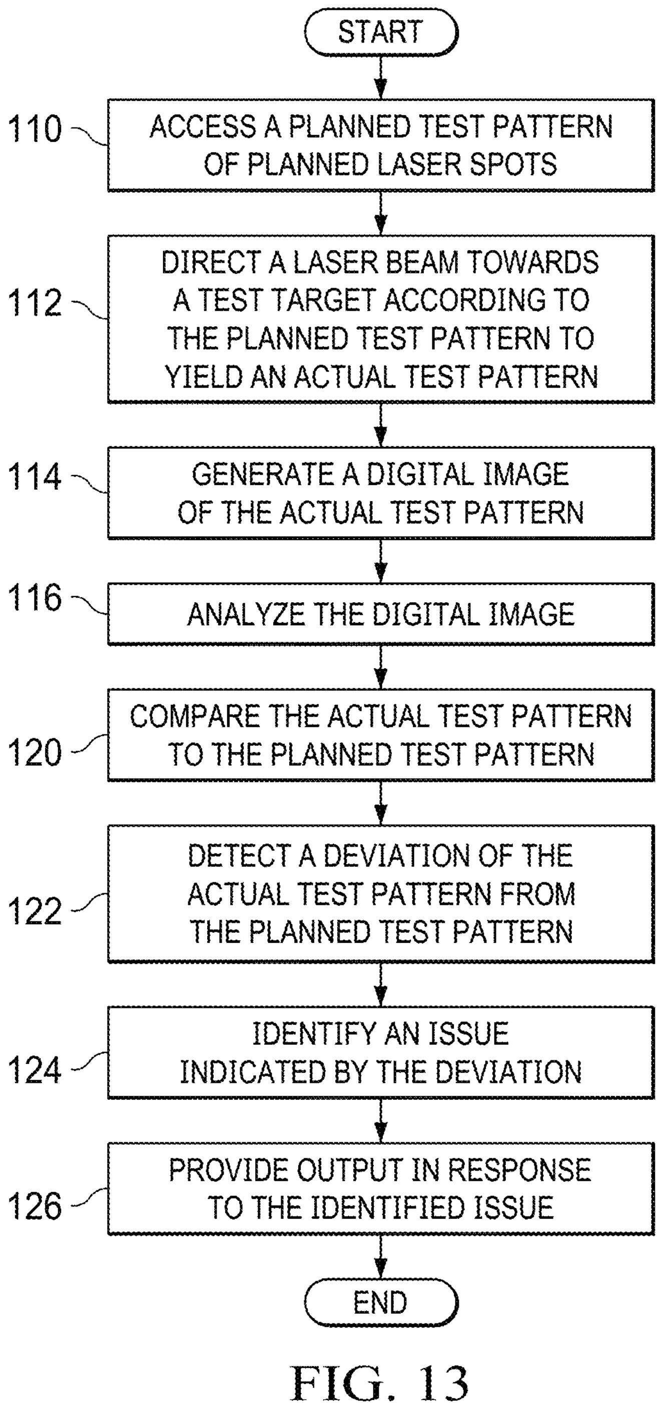
FIG. 13 illustrates an example of a method of detecting an issue with a laser system that may be performed by the system of FIG. 1, according to certain embodiments.

FIG. 13 illustrates an example of a method of detecting an issue with a laser system 20 that may be performed by system 10 of FIG. 1, according to certain embodiments. In the embodiments, the method starts at step 110, where laser system 20 accesses a planned test pattern of planned laser and/or planned auxiliary spots. At step 112, laser system 20 directs a laser beam towards a test target 12 located at the target plane 14 according to the planned test pattern to yield an actual test pattern of actual laser and/or actual auxiliary spots on test target 12. Imaging system 22 generates a digital image of the actual test pattern at step 114.

Computer 24 analyzes the digital image at step 116 to prepare to perform one or more of steps 120 to 126. In certain embodiments, computer 24 may analyze the digital image by: determining grayscale values of the pixels of the digital image; identifying the subset of the grayscale values that represent the actual spots; and ascertaining the actual test pattern using the subset of grayscale values. In certain embodiments, computer 24 may also measure a dimension present in the actual test pattern using a mathematical relationship between length and pixels of the digital image.

Computer 24 compares the actual test pattern to the planned test pattern at step 120. In an example, the planned test pattern describes spot locations in length units, and the digital image describes spot locations in pixels. Using a mathematical relationship between length and pixels, computer 24 converts the spot locations in pixels to locations in length units to compare the patterns in order to detect deviations in the spot locations or the spots themselves.

Computer 24 detects a deviation of the actual from the planned test pattern at step 122 and identifies an issue indicated by the deviation at step 124. For example, the planned test pattern may have orthogonal axes, and the actual test pattern may have axes that are not orthogonal. This may indicate that mirrors of the scanner are misaligned or that the laser beam and target plane are misaligned. As another example, the actual test pattern may have laser spots not at the spot separation defined by the planned test pattern, which may indicate that the scanner is not directing the laser beam to the correct spots. As another example, the actual test pattern may have a different shape than defined by the planned test pattern, which may indicate that the laser beam and target plane are misaligned or that the scanner cannot properly guide the laser beam. As another example, an actual laser spot may have a different size or shape than a planned laser spot, which may indicate that a laser beam control device is not properly guiding the beam or that the laser beam and target plane are misaligned. As another example, the actual test pattern may be blurry, which may indicate that the laser system is experiencing unwanted vibration or that a beam control device cannot properly focus the beam.

Computer 24 provides output at step 126 in response to identifying the issue. In certain embodiments, the output may provide a warning indicating a problem with laser system 20 and/or send a command to laser system 20 that addresses the issue. For example, computer 24 may display a message describing the issue. As another example, computer 24 may calculate a correction to remove the deviation and generate a command to instruct optical devices 34 and/or scanner 32 to implement the correction.

Figure 14:
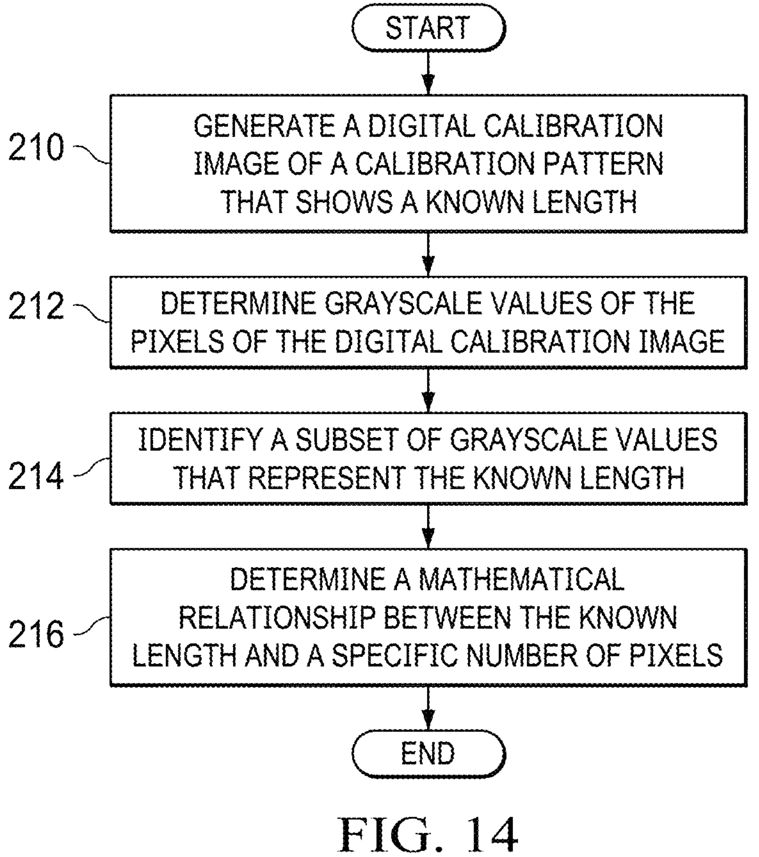
FIG. 14 illustrates an example of a method of determining a mathematical relationship between length and pixels that may be performed by the system of FIG. 1, according to certain embodiments.

FIG. 14 illustrates an example of a method of determining a mathematical relationship between length and pixels that may be performed by system 10 of FIG. 1, according to certain embodiments. In the embodiments, the method starts at step 210, where imaging system 22 generates a digital image of a calibration pattern that shows a known length, e.g., q units of length. The calibration pattern may be, e.g., a line with segments of the known length or a grid with squares having sides of the known length (e.g., the chessboard pattern shown in FIG. 12A).

Computer 24 determines grayscale values of the pixels of the digital calibration image at step 212. Computer 24 identifies the subset of grayscale values that represent the known length at step 214 and determines a mathematical relationship between the known length and a specific number of pixels at step 216. In the example, the known length extends across p pixels, i.e., p pixels correspond to the q length units, so the relationship is p pixels equals q length units. Computer 24 may use the length-pixel relationship for any suitable purpose, e.g., to convert the length of a dimension (e.g., spot separation) found in a digital image of laser spots from the number of pixels to length units.

A component (such as computer 24) of the systems and apparatuses disclosed herein may include an interface, logic, and/or memory, any of which may include computer hardware and/or software. An interface can receive input to the component and/or send output from the component, and is typically used to exchange information between, e.g., software, hardware, peripheral devices, users, and combinations of these. A user interface is a type of interface that a user can utilize to communicate with (e.g., send input to and/or receive output from) a computer. Examples of user interfaces include a display, Graphical User Interface (GUI), touchscreen, keyboard, mouse, gesture sensor, microphone, and speakers. Components of the systems and apparatuses may communicate with each other via computer interconnections, which may utilize wired, wireless, optical, or other technologies.

Logic can perform operations of the component. Logic may include one or more electronic devices that process data, e.g., execute instructions to generate output from input. Examples of such an electronic device include a computer, processor, microprocessor (e.g., a Central Processing Unit (CPU), including a multi-processor chip), and computer chip. Logic may include computer software that encodes instructions capable of being executed by an electronic device to perform operations. Examples of computer software include a computer program, application, and operating system.

A memory can store information and may comprise tangible, computer-readable, and/or computer-executable storage medium. Examples of memory include computer memory (e.g., Random Access Memory (RAM) or Read Only Memory (ROM)), mass storage media (e.g., a hard disk), removable storage media (e.g., a Compact Disk (CD) or Digital Video or Versatile Disk (DVD)), database, network storage (e.g., a server), and/or other computer-readable media. Particular embodiments may be directed to memory encoded with computer software.

Although this disclosure has been described in terms of certain embodiments, modifications (such as changes, substitutions, additions, omissions, and/or other modifications) of the embodiments will be apparent to those skilled in the art. Accordingly, modifications may be made to the embodiments without departing from the scope of the invention. For example, modifications may be made to the systems and apparatuses disclosed herein. The components of the systems and apparatuses may be integrated or separated, or the operations of the systems and apparatuses may be performed by more, fewer, or other components, as apparent to those skilled in the art. As another example, modifications may be made to the methods disclosed herein. The methods may include more, fewer, or other steps, and the steps may be performed in any suitable order, as apparent to those skilled in the art.

To aid the Patent Office and readers in interpreting the claims, Applicants note that they do not intend any of the claims or claim elements to invoke 35 U.S.C. § 112 (f), unless the words "means for" or "step for" are explicitly used in the particular claim. Use of any other term (e.g., "mechanism," "module," "device," "unit," "component," "element," "member," "apparatus," "machine," "system," "processor," or "controller") within a claim is understood by the applicants to refer to structures known to those skilled in the relevant art and is not intended to invoke 35 U.S.C. § 112(f).

What is claimed:

1. An ophthalmic laser system, comprising:

a laser system configured to:

access a planned test pattern of a planned laser spot, the planned laser spot having one or more planned beam features; and direct a laser beam towards a test target located at a target plane according to the planned test pattern to yield an actual test pattern of an actual laser spot on the test target, the actual laser spot corresponding to the planned laser spot, the actual laser spot having one or more actual beam features, the laser system comprising:

a laser source configured to generate the laser beam; and one or more beam control devices configured to guide the laser beam towards the test target;

an imaging system comprising one or more digital cameras configured to generate a digital image of the actual test pattern of the actual laser spot; and a computer configured to analyze the digital image to:

compare the actual laser spot to the planned laser spot;

detect one or more deviations of the one or more actual beam features from the one or more planned beam features;

identify one or more issues indicated by the one or more deviations; and provide output in response to the one or more issues.

2. The ophthalmic laser system of claim 1, wherein the computer is configured to analyze the digital image by:

determining a plurality of grayscale values of a plurality of pixels of the digital image;

identifying a subset of the plurality of grayscale values that represent the actual laser spot; and ascertaining the one or more actual beam features of the actual laser spot according to the subset of the plurality of grayscale values that represent the actual laser spot.

3. The ophthalmic laser system of claim 1, wherein the computer is configured to analyze the digital image by:

ascertaining a dimension of the actual laser spot according to a mathematical relationship between length and a number of a plurality of pixels of the digital image.

4. The ophthalmic laser system of claim 1, wherein the computer is configured to analyze the digital image by:

ascertaining a length of each diameter chord of one or more diameter chords of the actual laser spot.

5. The ophthalmic laser system of claim 1, wherein the computer is configured to analyze the digital image by:

ascertaining a first length of a first diameter chord of the actual laser spot; and ascertaining a second length of a second diameter chord of the actual laser spot, the second diameter chord orthogonal to the first diameter chord.

6. The ophthalmic laser system of claim 1, wherein the computer is configured to detect the one or more deviations of the one or more actual beam features from the one or more planned beam features by:

ascertaining an actual diameter of the actual laser spot;

comparing the actual diameter to a planned diameter of the planned laser spot; and determining whether the actual diameter differs from the planned diameter.

7. The ophthalmic laser system of claim 1, wherein the computer is configured to detect the one or more deviations of the one or more actual beam features from the one or more planned beam features by:

ascertaining an actual shape of the actual laser spot;

comparing the actual shape to a planned shape of the planned laser spot; and determining whether the actual shape differs from the planned shape.

8. The ophthalmic laser system of claim 1, wherein the computer is configured to detect the one or more deviations of the one or more actual beam features from the one or more planned beam features by:

ascertaining an actual sharpness of the actual laser spot;

comparing the actual sharpness to a planned sharpness of the planned laser spot; and determining whether the actual sharpness differs from the planned sharpness.

9. The ophthalmic laser system of claim 1, wherein the computer is configured to identify the one or more issues indicated by the one or more deviations by:

identifying a beam control device of the one or more beam control devices that fails to properly guide the laser beam to the test target.

10. The ophthalmic laser system of claim 9, wherein the computer is configured to provide the output in response to the one or more issues by:

instructing the beam control device to properly guide the laser beam to the test target.

11. The ophthalmic laser system of claim 1, wherein the computer is configured to identify the one or more issues indicated by the one or more deviations by:

determining that the laser beam is misaligned with the target plane.

12. The ophthalmic laser system of claim 11, wherein the computer is configured to provide output in response to the one or more issues by:

instructing the laser system to align the laser beam with the target plane.

13. The ophthalmic laser system of claim 1, wherein the computer is configured to provide the output in response to the one or more issues by:

providing a warning indicating a problem with the laser system.

14. The ophthalmic laser system of claim 1, wherein the computer is configured to provide the output in response to the one or more issues by:

sending a command to the laser system that addresses at least one issue of the one or more issues.

15. The ophthalmic laser system of claim 1, wherein the computer is configured to provide the output in response to the one or more issues by:

calculating a correction to remove a deviation of the one or more deviations; and generating a command to instruct the laser system to implement the correction.

16. The ophthalmic laser system of claim 1, the imaging system comprising a digital microscope.

17. The ophthalmic laser system of claim 1, the computer further configured to:

access a plurality of previous actual test patterns;

analyze the plurality of previous actual test patterns; and detect a trend of a previous issue with the laser system in accordance with the plurality of previous actual test patterns.

18. The ophthalmic laser system of claim 1, wherein:

the one or more digital cameras are configured to generate a digital calibration image of a calibration pattern that shows a known length; and the computer is configured to determine a mathematical relationship between the known length and a number of a plurality of pixels of the digital calibration image.

19. The ophthalmic laser system of claim 18, wherein the computer is configured to determine the mathematical relationship by:

determining a plurality of calibration grayscale values of the plurality of pixels of the digital calibration image;

identifying a subset of the plurality of calibration grayscale values that represent the known length; and determining the mathematical relationship between the known length and the number of the plurality of pixels according to the subset of the plurality of calibration grayscale values that represent the known length.

* * * * *